US005118684A

United States Patent [19]

Sugimoto et al.

[11] Patent Number: 5,118,684

[45] Date of Patent: Jun. 2, 1992

[54] PIPERDINE DERIVATIVE AND PHARMACEUTICAL COMPOSITION

[75] Inventors: Hachiro Sugimoto, Ushiku; Takaharu Nakamura, Abiko; Yutaka Tsuchiya, Ushiku; Hiroyuki Sugumi, Yatabemachi; Kunizou Higurashi, Tokyo; Norio Karibe, Yatabemachi; Yoshiharu Yamanishi, Ryugasaki; Hiroo Ogura, Tsuchiura; Shin Araki; Atsuhiko Kubota, both of Sakuramura; Michiko Ohtake, Mitsukaido; Kiyomi Tamatsu, Kamakura, all of Japan

[73] Assignee: Eisai Co., Ltd., Tokyo, Japan

[21] Appl. No.: 679,769

[22] Filed: Apr. 3, 1991

Related U.S. Application Data

[62] Division of Ser. No. 479,948, Feb. 14, 1990, Pat. No. 5,039,681, which is a division of Ser. No. 321,624, Mar. 10, 1989, Pat. No. 4,942,169, which is a division of Ser. No. 946,459, Dec. 24, 1986, Pat. No. 4,849,431.

[30] Foreign Application Priority Data

Dec. 27, 1985 [JP] Japan .............................. 60-293885

[51] Int. Cl.[5] .................. A61K 31/495; C07D 521/00

[52] U.S. Cl. .................................... 514/249; 544/285; 544/350; 544/406; 546/79; 546/99; 546/113; 546/142; 546/169; 546/187; 546/194; 546/197; 546/198; 546/201; 546/206; 546/232; 546/234

[58] Field of Search ......................... 544/350; 514/249

[56] References Cited

U.S. PATENT DOCUMENTS 5,041,547 8/1991 Miller et al. ....................... 544/350

*Primary Examiner*—Alan L. Rotman
*Assistant Examiner*—James H. Turnipseed
*Attorney, Agent, or Firm*—Flynn, Thiel, Boutell & Tanis

[57] ABSTRACT

A novel piperidine derivative is defined by the formula (I), including a slt thereof, $R^1—X—(A)—R^2$ (I)

wherein $R^1$ denotes a univalent group derived from one selected among substituted or unsubstituted benzene, pyridine, pyrazine, indole, anthraquinone, quinoline, substituted or unsubstituted phthalimide, homophthalimide, pyridinecarboxylic acid imide, pyridine N-oxide, pyrazinedicarboxylic acid imide, naphthalenedicarboxylic acid imide, substituted or unsubstituted quinazolinedione, 1,8-naphthalimide, bicyclo [2.2.2] oct-5-ene-2,3-dicarboxylic acid imide and pyromerylimide, X denotes a group of the formula $—(CH_2)_n—$, a group of the formula $—O(CH_2)_n—$, a group of the formula $—S(CH_2)_n—$, a group of the formula $—NH(CH_2)_n—$, a group of the formula $—SO_2NH(CH_2)_n—$, a group of the formula

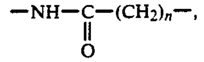

a group of the formula

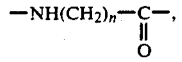

a group of the formula

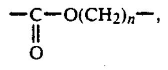

a group of the formula $—CH_2NH(CH_2)_n—$, a group of the formula

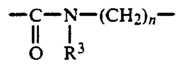

(in all the above formulas, n is an integer of 1 through 7 and $R^3$ represents a lower alkyl group or a benzyl group), a group of the formula

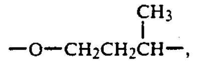

a group of the formula

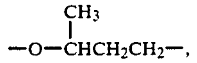

a group of the formula $—O—CH_2CH_2CH=$ or a group of the formula

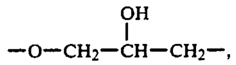

the ring A denotes a group of the formula

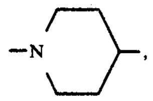

a group of the formula

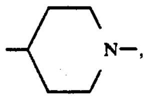

a group of the formula (Abstract continued on next page.)

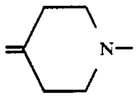
or a group of the formula
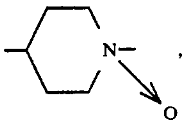
,
and
$R^2$ denotes a hydrogen atom, a lower alkyl group, a substituted or unsubstituted benzyl group, a substituted or unsubstituted benzoyl group, a pyridyl group, a 2-hydroxyethyl group, a pyridylmetyl group or a group of the formula
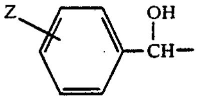
(wherein Z represents a halogen atom).
15 Claims, No Drawings

PIPERDINE DERIVATIVE AND PHARMACEUTICAL COMPOSITION

This is a division of Ser. No. 07/479,948, filed Feb. 14, 1990, now U.S. Pat. No. 5,039,681, which is a division of Ser. No. 07/321,624, filed Mar. 10, 1989, now U.S. Pat. No. 4,942,169, issued Jul. 17, 1990, which is a division of Ser. No. 06/946,459, filed Dec. 24, 1986, now U.S. Pat. No. 4,849,431, issued Jul. 18, 1989.

The present invention relates to piperidine derivatives having excellent actions as medicines. The invention relates more particularly to piperidine derivatives of the following general formula (I) or pharmacologically allowable salts thereof:

$R^1$—X—Ⓐ—$R^2$ (I)

wherein $R^1$ denotes a univalent group derived from one selected among substituted or unsubstituted benzene, pyridine, pyrazine, indole, anthraquinone, quinoline, substituted or unsubstituted phthalimide, homophthalimide, pyridinecarboxylic acid imide, pyridine N-oxide, pyrazinedicarboxylic acid imide, naphthalenedicarboxylic acid imide, substituted or unsubstituted quinazolinedione, 1,8-naphthalimide, bicyclo [2.2.2] octo-5-ene-2,3-dicarboxylic acid imide and pyromerylimide, X denotes a group of the formula $—(CH_2)_n—$, a group of the formula $—O(CH_2)_n—$, a group of the formula $—S(CH_2)_n—$, a group of the formula $—NH(CH_2)_n—$, a group of the formula $—SO_2NH(CH_2)_n—$, a group of the formula

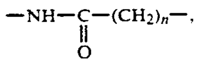

a group of the formula

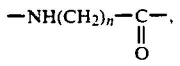

a group of the formula

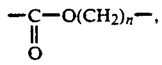

a group of the formula $—CH_2NH(CH_2)_n—$, a group of the formula

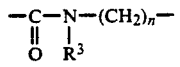

(in all the above formulas, n is an integer of 1 through 7 and $R^3$ represents hydrogen a lower alkyl group or a benzyl group), a group of the formula

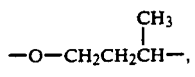

a group of the formula

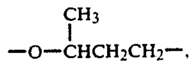

a group of the formula $—O—CH_2CH_2CH=$ or a group of the formula

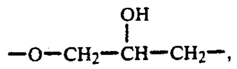

the ring A denotes a group of the formula

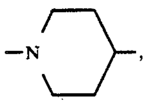

a group of the formula

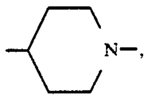

a group of the formula

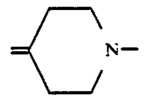

or a group of the formula

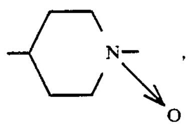

and $R^2$ denotes a hydrogen atom, a lower alkyl group, a substituted or unsubstituted benzyl group, a substituted or unsubstituted benzoyl group, a pyridyl group, a 2-hydroxyethyl group, a pyridylmethyl group or a group of the formula

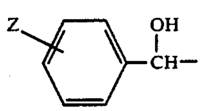

(wherein Z represents a halogen atom).

The lower alkyl group in the definition of the formula (I) means a straight-chain or branched alkyl group having 1 to 6 carbon atoms, such as methyl, ethyl, n-propyl, isopropyl, n-butyl, isobutyl, 1-methylpropyl, tert-butyl, n-pentyl, 1-ethylpropyl, isoamyl or n-hexyl. Preferable lower alkyl groups include a methyl group, ethyl group, etc. The lower alkoxy group means a group derived from the above lower alkyl group.

The univalent group derived from substituted or unsubstituted benzene in the definition of $R^1$ means specifically the following:

(1) Univalent group of the formula

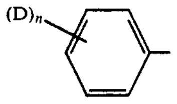

wherein n is an integer of 1 through 3 and D denotes a substituent group or two or three of the same or different substituent groups selected from the group consisting of a hydrogen atom, a lower alkyl group, a nitro group, a lower alkoxy group, an alkylenedioxy group formed between adjacent carbon atoms in arbitrary positions, a cyano group, a halogen atom, an amino group, a monoalkylamino or dialkylamino group, a lower alkoxycarbonyl group, a trifluoromethyl group, a formyl group, a hydroxy group (hydroxyl group), a lower alkylthio group, a lower alkylsulfinyl group, a lower alkylsulfonyl group, a lower alkylsulfoxide group, a lower alkylcarbonyl group, a methoxymethylthio group, a halogenomethylthio group, a cycloalkylsulfonyl group, a phenyl group phenoxy a cycloalkylthio group and a cyclohexenyloxy group.

(2) Univalent group of the formula

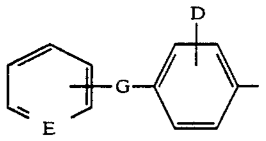

wherein G denotes a group of the formula $$-\overset{\overset{O}{\|}}{C}-,$$

a group of the formula $$-O-\overset{\overset{O}{\|}}{C}-,$$

a group of the formula —O—, a group of the formula $$-CH_2-NH-\overset{\overset{O}{\|}}{C}-,$$

a group of the formula $-CH_2-O-$, a group of the formula $-CH_2-SO_2-$, a group of the formula $$-\underset{\underset{OH}{|}}{CH}-$$

or a group of the formula $$-CH_2-\overset{\overset{O}{\uparrow}}{S}-,$$

E denotes a carbon atom or a nitrogen atom, and D has the same meaning as defined in (I).

In the univalent group derived from substituted or unsubstituted phthalimide in the definition of $R^1$, the examples of the preferable substituent include a nitro group, an amino group, a halogen group, a lower alkyl group, a lower alkoxy group, a hydroxy group, a benzoyl group, a phenylcarbonyl group, a phenylcarbonylamino group, a lower alkylcarbonylamino group, a hydroxycarbonyl group, a benzylaminocarbonyl group and a dialkylaminocarbonyl group. The univalent group may be substituted by two or more same or different substituents if necessary.

In the univalent group derived from substituted or unsubstituted quinazolinedione in the definition of $R^1$, the examples of the preferable substituent include a lower alkyl group and a halogen group.

Preparation Method A $$\underset{(II)}{R^1-X-Hal} + \underset{(III)}{H-(A)-R^2} \longrightarrow \underset{(I)}{R^1-X-(A)-R^2}$$

wherein Hal denotes a halogen atom, and $R^1$, X, $R^2$ and the ring A have the same meaning as defined above.

Namely, a compound of the general formula (II) (wherein Hal denotes a chlorine atom, bromine atom, iodine atom, etc. and among them the bromine atom is most preferable) and a piperidine derivative of the general formula (III) are subjected to a condensation reaction by a conventional method, preferably in the presence of a base such as sodium hydrogencarbonate, sodium carbonate, potassium carbonate or triethylamine, to obtain the final compound (I). In this case, as an organic solvent there is used, for example, benzene, toluene, ethanol, butanol or dimethylformamide (DMF).

Preparation Method B

In the case where X denotes a group of the formula $$-\overset{\overset{O}{\|}}{C}-\overset{\overset{R^3}{|}}{N}-(CH_2)_n-$$

in the general formula (I)

$$\underset{(IV)}{R^1-\overset{\overset{O}{\|}}{C}-Hal} + \underset{(V)}{H\overset{\overset{R^3}{|}}{N}-(CH_2)_n-(A)-R^2} \longrightarrow$$

$$\underset{(VI)}{R^1-\overset{\overset{O}{\|}}{C}-\overset{\overset{R^3}{|}}{N}(CH_2)_n-(A)-R^2}$$

Namely, an acid halogenide of the general formula (IV) is allowed to react with a piperidine derivative of the general formula (V) in an organic solvent such as chloroform, benzene, toluene, dioxane, tetrahydrofuran or dimethylformamide (DMF), in the presence of a desalting agent such as sodium carbonate, potassium carbonate, sodium hydroxide, potassium hydroxide or triethylamine, with ice-cooling, at room temperature or with heating, to easily obtain the compound (VI), one of the final compounds.

Preparation Method C

In the case where X denotes a group of the formula $-SO_2-NH(CH_2)_n-$ in the general formula (I)

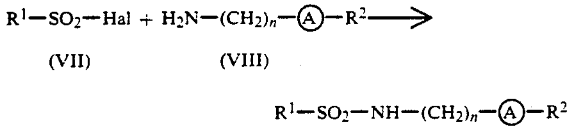

(VII) (VIII)

(IX)

Procedure similar to that of Preparation Method B is used to obtain the compound (IX), one of the final compounds.

Preparation Method D

In the case where $R^1$ denotes a univalent group derived from imide selected among substituted phthalimide, homophthalimide, pyridinecarboxylic acid imide, pyrazinedicarboxylic acid imide, naphthalenedicarboxylic acid imide, 1,8-naphthalimide, bicyclo [2.2.2] octo-5-ene-2,3-dicarboxylic acid imide and pyromerylimide and X denotes a lower alkylene group in the general formula (I)

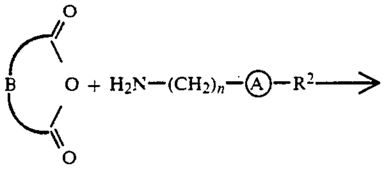

(X) (XI)

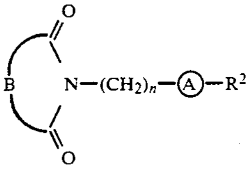

(XI)

wherein n is an integer of 1 through 7 and B denotes a residue after the removal of a group of the formula

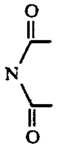

in all the above-defined $R^1$.

Namely, an acid anhydride of the general formula (X) and a piperidine derivative of the general formula (XI) are subjected to a condensation reaction by a conventional method to obtain the compound (XII), one of the object substances.

The reaction is carried out with application of heat in an organic solvent such as, for example, ethanol, butanol, dioxane, dimethylformamide (DMF) or acetic anhydride.

Preparation Method E

In the case where $R^1$ denotes a univalent group derived from substituted quinazolinedione and X denotes a lower alkylene group.

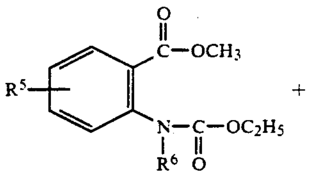

(XIII)

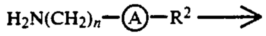

(XIV)

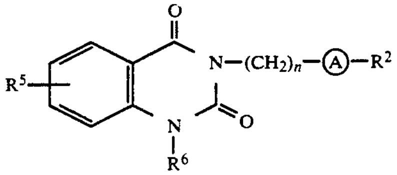

(XV)

$R^5$ and $R^6$ are hydrogen, or a substituent such as a lower alkyl and a halogen.

Namely, a diester of the general formula (XIII) is allowed to react with a piperidine derivative of the general formula (XIV), with application of heat, in a suitable solvent which does not participate in the reaction or in the absence of the solvent, to obtain the quinazolone compound (XV), one of the object substances.

Preparation Method F

In the case where $R^1$ denotes a univalent group derived from substituted or unsubstituted benzene and X denotes a group of the formula $-O(CH_2)_n-$ in the general formula (I)

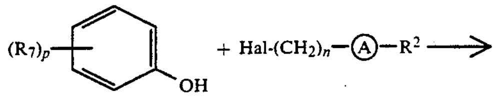

(XVI) (XVII)

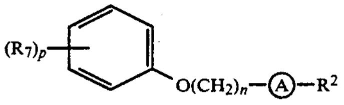

(XVIII)

$R^7$ is hydrogen or a phenyl defined above. p is zero or an integer of 1 to 3.

Namely, a phenol derivative of the general formula (XVI) and a halogen compound of the general formula (XVII) are subjected to a condensation reaction by a conventional method to obtain the compound (XVIII), one of the final compounds.

The reaction is carried out in a solvent such as, for example, tetrahydrofuran or dimethylformamide (DMF), in the presence of NaH or NaOH, at room temperature or with heating, thereby obtaining a good result.

Preparation Method G

In the case where $R^1$ denotes a univalent group derived from substituted or unsubstituted benzene and X denotes a group of the formula $—S(CH_2)_n—$ in the general formula (I)

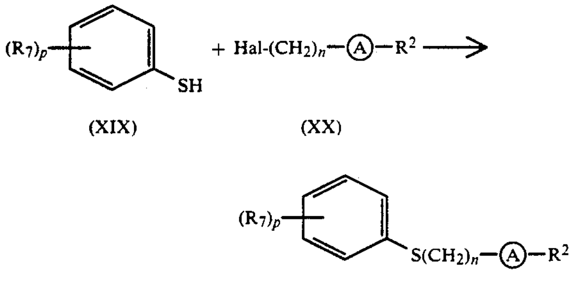

(XIX) (XX)

(XXI)

Procedure similar to that of Preparation Method F is used to obtain the compound (XXI), one of the object substances.

Preparation Method H $R^1—X—OH + H—Ⓐ—R^2 \longrightarrow$ (XXII) (III)

$R^1—X—Ⓐ—R^2$ (I)

wherein $R^1$, X, $R^2$ and the ring A have the same meaning as defined above.

Namely, a compound of the general formula (XXII) and a piperidine derivative of the general formula (III) are subjected to a condensation reaction preferably using a desalting agent such as triethylamine, N-methylmorpholine or N,N'-dimethylaniline to obtain the object substance (I).

In this case, benzene, toluene, tetrahydrofuran, dimethylformamide or dioxane is used as a solvent.

Various attempts have been made to treat for middle-age dementia, senile dementia and so on with medicines. At present, however, there is no medicine which is considered to be drastically effective for the diseases. Considered to be effective at present are anticholinesterase agents (example; physostygumine). The physostygumine, however, suffers disadvantages: action of short duration, strong side effects, and so forth.

Accordingly, the inventors have been making many intensive studies over a long term of years in order to develop medicines having actions of long duration and being high in safety.

As a result, they have discovered that the piperidine derivatives of the general formula (I) can attain the desired end.

Specifically, the compounds of the structural formula (I) according to the invention have the following important features. They have strong and highly-selective antiacetylcholinesterase activities. Furthermore, they increase the amount of acetylcholine in the brain and are effective for the model of retentive disorder. In addition, they have actions of long duration and are high in safety, compared with the physostygumine heretofore in use in the field. Thus, the invention is of great value.

Namely, the compounds of the invention are piperidine derivatives of the following general formula (I) or pharmacologically allowable salts thereof:

$R^1—X—Ⓐ—R^2$ (I)

wherein $R^1$ denotes a univalent group derived from one selected among substituted or unsubstituted benzene, pyridine, pyrazine, indole, anthraquinone, quinoline, substituted or unsubstituted phthalimide, homophthalimide, pyridinecarboxylic acid imide, pyridine N-oxide, pyrazinedicarboxylic acid imide, naphthalenedicarboxylic acid imide, substituted or unsubstituted quinazolinedione, 1,8-naphthalimide, bicyclo [2.2.2] octo-5-ene-2,3-dicarboxylic acid imide and pyromerylimide, X denotes a group of the formula $—(CH_2)_n—$, a group of the formula $—O(CH_2)_n—$, a group of the formula $—S(CH_2)_n—$, a group of the formula $—NH(CH_2)_n—$, a group of the formula $—SO_2NH(CH_2)_n—$, a group of the formula

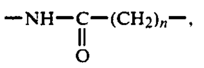

a group of the formula

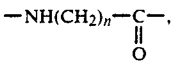

a group of the formula

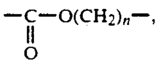

a group of the formula $—CH_2NH(CH_2)_n—$, a group of the formula

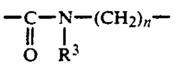

(in all the above formulas, n is an integer of 1 through 7 and $R^3$ represents a lower alkyl group or a benzyl group), a group of the formula

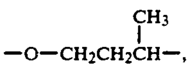

a group of the formula

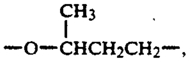

a group of the formula $—O—CH_2CH_2CH=$ or a group of the formula

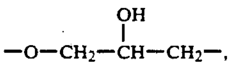

the ring A denotes a group of the formula

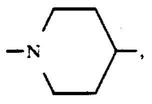

a group of the formula

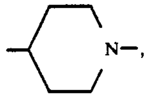

a group of the formula

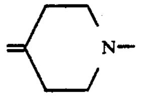

or a group of the formula

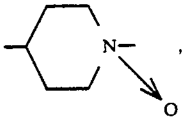

and $R^2$ denotes a hydrogen atom, a lower alkyl group, a substituted or unsubstituted benzyl group, a substituted or unsubstituted benzoyl group, a pyridyl group, a 2-hydroxyethyl group, a pyridylmethyl group or a group of the formula

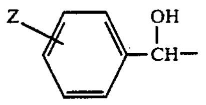

(wherein Z represents a halogen atom).

Therefore the purposes of the invention are to provide a novel compound which is effective for treating various types of dementias and sequelae of cerebrovascular diseases methods for preparation of the compound and a pharmaceutical composition comprising the compound as the effective ingredient.

The pharmacologically acceptable salt, to use in the invention includes for instance an inorganic salt such as hydrochloride, sulfate, hydrobromate or phosphate, and an organic salt such as formate, acetate, trifluoroacetate, maleate, tartrate, methanesulfonate, benzenesulfonate or toluenesulfonate.

The compound of the invention is effective for the treatment, prevention, remission and improvement of various types of senile dementia, especially senile dementia of the Alzheimer type or Alzheimer's disease, the disturbance of attention, aphasia, hypobulia, emotional disorder, memory disorder, hallucinatory-paranoid state and abnormal behavior, accompanying and following cerebrovascular diseases such as cerebral apoplexy (cerebral hemorrhage, cerebral infarction), sequelae of encephalitis and cerebral palsy.

Further, the compound of the invention has a strong, highly selective anticholinesterase activity and is eventually useful as a medicine based on that activity.

When the compound is used as the medicine, it may be orally or parenterally administered. It is parenterally administered in the form of an intravenous, hypodermic or intramuscular injection or a suppository. It may be administered also in the form of a sublingual tablet. The dose of the administration depends on conditions of the patient, such as age, sex, a body weight and sensitivity, the method of the administration such as times and intervals, properties, preparation and kind of the medicine, kind of effective ingredients, and in case another treatment is also effected simultaneously the kind, frequency and intended effects of the treatment. In general, a dose of the administration is about 0.1 to 300 mg, preferably about 1 to 100 mg, for an adult. The administration with the amount is made one to four times a day.

When the compounds of the invention are prepared into medicines, they are prepared into medicines in the form of injections, suppositories, sublingual tablet, tablets, capsules, etc. using ordinary carrier by a conventional method in the technical field of preparation.

In the preparation of injections, pH regulator, buffer, suspending agent, dissolution adjuvant, stabilizer, preservative, etc. are added to the principal ingredient when required, and intravenous, hypodermic and intramuscular injections are prepared by a conventional method. In this case, the injections may be frozen and dried, if necessary, by a conventional method.

Examples of the suspending agent include methyl cellulose, polysorbate 80, hydroxyethyl cellulose, gum arabic, tragacanth powder, carboxymethyl cellulose sodium, polyoxyethylene sorbitan monolaurate, etc.

Examples of the dissolution adjuvant include polyoxyethylene-hardened castor oil, polysorbate 80, amide nicotinate, polyoxyethylene sorbitan monolaurate, castor oil fatty acid ethyl ester, etc.

Examples of the stabilizer include sodium sulfite, sodium metasulfite, ether, etc. Examples of the preservative include methyl paraoxybenzoate, ethyl paraoxybenzoate, sorbic acid, phenol, cresol, chlorocresol, etc.

The representative compounds of the invention will be described hereinafter by way of examples. It goes without saying, however, that the representative compounds are for purpose of help to the understanding of the invention and are not intended as a definition of the limits of the invention.

The values of NMR in the following examples are those in free substances.

EXAMPLE 1

1-benzyl-4-[γ-(4-nitrophenoxy) propyl] piperidine.hydrochloride

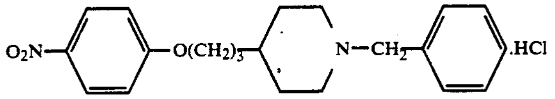

0.8 g of p-nitrophenol and 1.4 g of N-benzyl-4-(γ-bromopropyl)-piperidine are dissolved in 20 ml of dimethylformamide (DMF). To the mixed solution is added, little by little, with stirring at room temperature, 0.3 g of 60% sodium hydride.

Hereafter, the resulting mixture is stirred for 2 hours at room temperature and is further stirred for about 6 hours and 30 minutes at 70° to 80° C. After the solvent is distilled off under reduced pressure, an aqueous chloroform-5% caustic soda solution is added to the residue followed by shaking sufficiently with a separating funnel to separate out a chloroform layer.

The chloroform layer is washed with a saturated saline solution, which is then dried over magnesium sulfate. Chloroform is distilled off under reduced pressure, and the resulting residue is purified using a silica gel column. The distillation is performed using 2% methanol-chloroform. After distilling off the solvent under reduced pressure, the residue is dissolved in ethyl acetate followed by adding a 10% hydrochloric acid-ethyl acetate solution to separate out crystals. Upon recrystallization from ethanol-water-ethyl ether, 1.9 g (yield: 84.1%) of the titled compound having the following physical properties is obtained.

Melting point (°C.): 229-230.

| Elemental analytical values: $C_{21}H_{26}N_2O_3.HCl$ | C | H | N |
|---|---|---|---|
| Theoretical value (%) | 64.52 | 6.96 | 7.17 |
| Found value (%) | 64.21 | 7.03 | 7.06 |

EXAMPLE 2

N-[4'-(1'-benzylpiperidine) ethyl]-4-benzylsulfonylbenzamide.hydrochloride

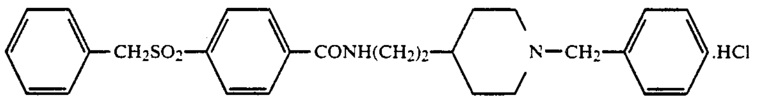

3 g of 1-benzyl-4-aminoethylpiperidine and 2.8 g of triethylamine are added to 100 ml of anhydrous tetrahydrofuran. 4.1 g of 4-benzylsulfonylbenzoylchloride is mixed with 50 ml of anhydrous tetrahydrofuran with ice-cooling and stirring, which is then added dropwise to the above mixed solution for about 20 minutes. The resulting mixture is stirred for about 20 minutes at room temperature and is further refluxed for about 20 minutes. Then, tetrahydrofuran is distilled off under reduced pressure. The resulting residue is purified using a column in a similar manner as in Example 1 and is formed into a hydrochloride by a conventional method to obtain 3.55 g of the titled compound (yield: 49.4%).

Melting point (°C.): 187-188.

| Elemental analytical values: $C_{28}H_{32}N_2O_3S.HCl$ | C | H | N |
|---|---|---|---|
| Theoretical value (%) | 65.55 | 6.48 | 5.46 |
| Found value (%) | 64.64 | 6.27 | 5.36 |
| 3/10 ($H_2O$) | 64.86 | 6.53 | 5.46 |

EXAMPLE 3

N-[4'-(1'-benzylpiperidine) ethyl]-4-isonicotinic acid amide.hydrochloride

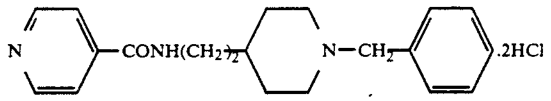

Preparation Example 1

2.4 g of isonicotinic acid chloride.hydrochloride is added little by little to 4.4 g of 1-benzyl-4-aminoethylpiperidine, 5.6 g of potassium carbonate and 50 ml of dioxane while they are cooled with ice and stirred. After the reaction for about 1 hour at room temperature, dioxane is distilled off under reduced pressure. To the resulting residue are added 50 ml of water and 20 ml of a 5% aqueous NaOH solution to alkalify the residue. The alkaline residue is then extracted with chloroform. After washing with water, the resulting chloroform layer is dried over potassium carbonate, and chloroform is distilled off under reduced pressure. The resulting residue is purified with 2% methanol-chloroform-based and 5% methanol-chloroform-based solvents by the use of a silica gel column, and is formed into a hydrochloride using a 10% hydrochloric acid-ethyl acetate solution to obtain 5.1 g of the titled compound (yield: 70.0%).

Preparation Example 2

4.7 g of isonicotinic acid is dissolved in a mixed solution of dimethylformamide-tetrahydrofuran (1/1). To the mixture are added, at −30° to −15° C., 3.85 g of N-methylformalin and 4.13 g of ethyl chlorocarbonate. The resulting mixture is stirred for 5 minutes at −15° C. Dimethylformamide-tetrahydrofuran solution of 8.33 g of N-benzylpiperidylethylamine is added to the reaction solution followed by stirring for 2 hours at 0° C. and then 1 hour at room temperature. After removing a precipitate by filtration, the resulting filtrate is concentrated, and the residue is dissolved in chloroform. After washing with caustic soda and water, the chloroform layer is dried over magnesium sulfate, and chloroform is distilled off. The resulting oily residue is purified using a silica gel chromato to obtain 9.5 g of the titled compound (yield: 77.0%).

NMR (δ value, DMSO): 1.14-2.04 (9H, m), 2.8-2.9 (2H, bd), 3.36-3.56 (2H, m), 3.44 (2H, s), 6.2 (1H, bt), 7.24 (5H, s), 7.54 (2H, m), 8.68 (2H, m).

EXAMPLE 4

N-methyl-N-[4'-(1'-benzylpiperidine) ethyl]-4-benzylsulfonylbenzamide.hydrochloride

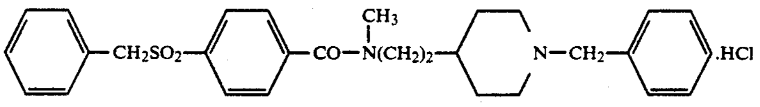

5.9 g of 4-benzylsulfonylbenzoylchloride is added little by little to 4.6 g of 1-benzyl-4-(N'-methylaminoethyl) piperidine, 5 g of triethylamine and 40 ml of chloroform while they are cooled with ice and stirred. After the reaction for 12 hours at room temperature, 20 ml of water and 20 ml of a 5% aqueous NaOH solution are added to the reaction solution followed by shaking sufficiently with a separating funnel to separate out a chloroform layer. After washing with water, the chloroform layer is dried over magnesium sulfate, and chloroform is distilled off under reduced pressure. The resulting residue is purified using a column in a similar manner as in Example 1 and is formed into a hydrochloride. Upon recrystallization from ethanol, 8.2 g of the titled compound is obtained (yield: 78.1%).

Melting point (°C.): 200–201.

| Elemental analytical values: $C_{20}H_{34}N_2O_3S$ | C | H | N |
|---|---|---|---|
| Theoretical value (%) | 66.08 | 6.69 | 5.31 |
| Found value (%) | 66.12 | 6.67 | 5.21 |

EXAMPLE 5

N-methyl-N-[4'-(1'-benzylpiperidyl) ethyl]isonicotinic acid amide hydrochloride

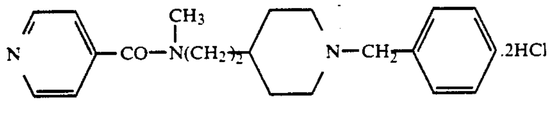

3.48 g of N-benzyl-4-(N'-methylaminoethyl) piperidine and 4.6 g of potassium carbonate are added to a mixed solution of 40 ml of chloroform and 10 ml of water. To the mixture is added, little by little, with ice-cooling and stirring, 3.2 g of isonicotinic acid chloride.hydrochloride.

After stirring for 1 hour at room temperature, 20 ml of water and 10 ml of an aqueous 1N-NaOH solution are added to the reaction solution, and a chloroform layer is separated out. After washing with water, the chloroform layer is dried over magnesium sulfate.

Chloroform is distilled off under reduced pressure to obtain 4.3 g of an oily matter. The oily matter is purified using a silica gel column in a similar manner as in Example 1 and is formed into a hydrochloride.

Upon recrystallization from acetone-ethanol, 4.0 g of the titled compound is obtained (yield: 72.0%).

| Elemental analytical values: $C_{21}H_{27}N_3O.2HCl.\frac{1}{2}H_2O$ | C | H | N |
|---|---|---|---|
| Theoretical value (%) | 60.14 | 7.21 | 10.12 |
| Found value (%) | 60.02 | 7.01 | 10.16 |

EXAMPLE 6

N-methyl-N-[4'-(1'-benzylpiperidine) ethyl]-4-cyclopentylsulfonylbenzamide.hydrochloride

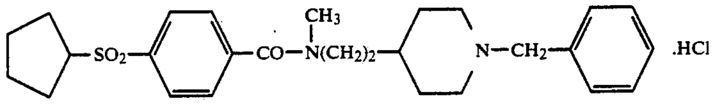

1.1 g of N-benzyl-4-(N'-methylaminoethyl) piperidine and 1.4 g of potassium carbonate are added to a mixed solution of 20 ml of chloroform and 5 ml of water. While stirring the mixture at room temperature, a solution in which 1.16 g of 4-cyclopentylsulfonylchloride is dissolved in 20 ml of chloroform is added dropwise to the mixture. After stirring for 2 hours at room temperature, 10 ml of water and 5 ml of an aqueous 1N-NaOH solution are added to the reaction solution, and a chloroform layer is separated out. After washing with water, the chloroform layer is dried over magnesium sulfate.

Chloroform is distilled off under reduced pressure to obtain a crude product. The crude product is purified using a silica gel column in a similar manner as in Example 1 and is formed into a hydrochloride.

Upon recrystallization from ethanol-ether, 1.9 g of the titled compound is obtained (yield: 80.0%).

Melting point (° C.): 234–236 (decomposition).

| Elemental analytical values: $C_{27}H_{36}N_2O_3S.HCl.\frac{1}{2}H_2O$ | C | H | N |
|---|---|---|---|
| Theoretical value (%) | 63.08 | 7.45 | 5.45 |
| Found value (%) | 63.10 | 7.25 | 5.40 |

EXAMPLE 7

N-[2-(N'-benzylpiperidino-4) ethyl]-4-nitrophthalimide.hydrochloride

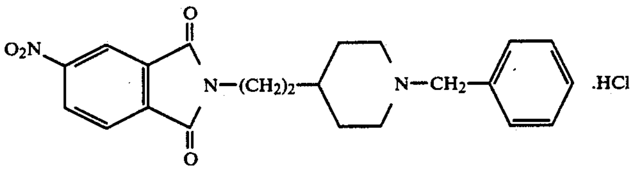

1.0 g of 4-nitro phthalic anhydride and 1.1 g of 4-(2-aminoethyl)-benzylpiperidine are added to 30 ml of dioxane. The resulting mixture is heated and refluxed for 2 hours.

The reaction solution is added with 50 ml of water followed by extracting with chloroform. The resulting chloroform layer is dried over magnesium sulfate, which is then concentrated to dryness under reduced pressure. The resulting residue is purified with a 5% ethanol-chloroform-based solvent by the use of a silica gel column to obtain 1.3 g of the object substance. The object substance is formed into a hydrochloride using a 10% hydrochloric acid-ethyl acetate solution. Upon recrystallization from acetone-isopropyl ether, 0.98 g of the titled compound is obtained (yield: 45.1%).

Melting point (° C.): 224–227.

| Elemental analytical values: $C_{22}H_{23}N_3O_4.HCl$ | C | H | N |
|---|---|---|---|
| Theoretical value (%) | 61.47 | 5.63 | 9.77 |
| Found value (%) | 61.35 | 5.69 | 10.01 |

EXAMPLE 8

N-[2-(N'-benzylpiperidino-4) ethyl]-2,3-pyrazinedicarboxylic acid imide

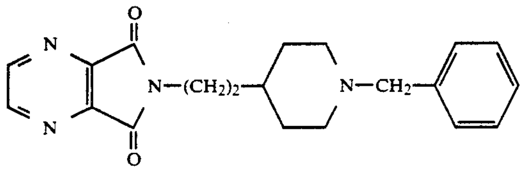

7.5 g of 2,3-pyrazinedicarboxylic anhydride and 12.0 g of 4-(2-aminoethyl)-benzylpiperidine are stirred for 10 minutes at 120° C. to form a brown tar-like mixture. After allowing to stand for cooling, 7 ml of acetic anhydride is added dropwise to the brown tar-like mixture at 80° C. followed by stirring for about 30 minutes at 100° C. The resulting tar-like substance is added with and dissolved in 20 ml of chloroform and is purified using a silica gel column in a similar manner as in Example 1. Since the object substance is not well separated out, the above tar-like substance is further purified by distillation with benzene and a 10% ethanol-benzene-based solvent, to obtain 5.9 g of the object compound as a yellow-brown oily matter (yield: 33.6%).

NMR (δ value, DMSO): 1.27–2.02 (9H, m), 2.8–2.9 (2H, bd), 3.46 (2H, s), 3.82 (2H, t), 7.26 (5H, s), 8.87 (2H, s).

EXAMPLE 9

N-[2-(N'-benzylpiperidino-4) ethyl]-1,8-naphthalimide

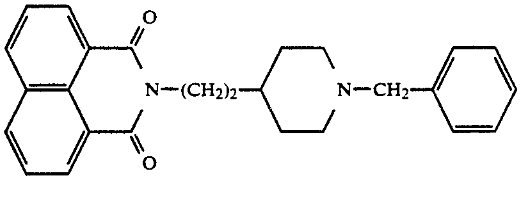

2 g of 1,8-naphthalic anhydride and 2.2 g of 4-(2-aminoethyl) benzylpiperidine are heated and refluxed in a solvent of n-butanol for 6 hours.

After allowing to stand for cooling, 50 ml of water is added to the reaction solution followed by extracting with chloroform. The resulting chloroform layer is dried over potassium carbonate, which is then concentrated to dryness under reduced pressure.

The oily residue thus obtained is purified with chloroform as a distilling solvent by the use of a silica gel column. The purified substance is formed into a hydrochloride using a 10% hydrochloric acid-ethanol solution. Upon recrystallization from ethanol-methanol, 2.0 g of the object compound is obtained (yield: 46%).

NMR (δ value, DMSO): 2.84 (2H, d), 3.45 (2H, s), 4.4 (2H, q), 7.24 (5H, s), 7.4 (2H, q), 8.1 (2H, dd), 8.5 (2H, dd).

EXAMPLE 10

3-[2-(1-benzyl-4-piperidino) ethyl]-2,4-(1H,3H)quinazolidione.hydrochloride

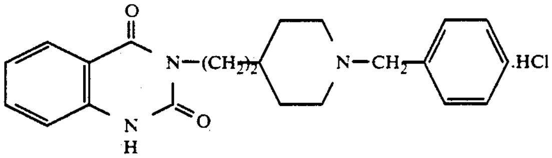

A mixture of 50 g of 2-[(ethoxycarbonyl) amino] benzoic acid methyl and 49 g of 4-(2-aminoethyl)benzylpiperidine is heated to 190° to 200° C. with stirring, and methanol and ethanol formed are distilled off.

After heating and stirring for about 6 hours, the mixture is purified using a silica gel column in a similar manner as in Example 1 and is formed into a hydrochloride.

Upon recrystallization from ethanol-water, 13.3 g of the titled compound is obtained (yield: 14.8%).

Melting point (° C.): 208–210.

| Elemental analytical values: $C_{22}H_{25}N_3O_2.HCl$ | C | H | N |
|---|---|---|---|
| Theoretical value (%) | 66.07 | 6.55 | 10.51 |
| Found value (%) | 66.02 | 6.64 | 10.75 |

EXAMPLES 11 TO 137

Compounds prepared using similar procedures as in Examples 1 to 10 are shown in Table 1 and Table 2.

The compounds shown in Tables 1 and 2 are represented by the formula $R^1$—X—Ⓐ—$R^2$

TABLE 1

$R^1$—X—(A)—$R^2$

| Example | $R^1$ | X | (A) | $R^2$ | Melting point (°C.) | Solvent for recrystallization | Molecular formula | Elemental analytical value (%) Upper column: Theoretical value (%) Bottom column: Found value (%) C | H | N | Preparation method |
|---|---|---|---|---|---|---|---|---|---|---|---|
| 11 | 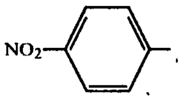 | $-O(CH_2)_2-$ | 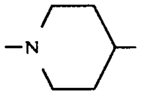 | 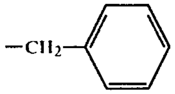 | 137~138.5 | EtOH—IPE | $C_{20}H_{24}N_2O_3.\frac{1}{4}H_2O.HCl$ | 62.98<br>62.85 | 6.74<br>6.65 | 7.34<br>7.16 | A |
| 12 | 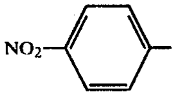 | $-O(CH_2)_2-$ | 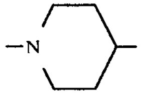 | H | 203~204 | EtOH | $C_{12}H_{15}N_2O_3.HCl$ | 54.44<br>54.38 | 6.68<br>6.64 | 9.77<br>9.57 | A |
| 13 | 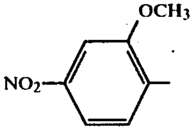 | $-O(CH_2)_3-$ | 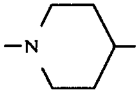 | 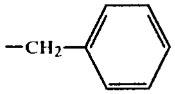 | 100~101 | EtOH—IPE | $C_{22}H_{28}N_2O_4$ | 68.73<br>68.50 | 7.34<br>7.61 | 7.29<br>7.38 | A |
| 14 | 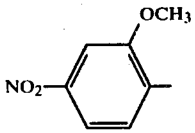 | $-O(CH_2)_3-$ | 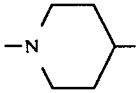 | 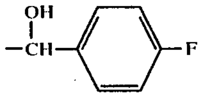 | 170~176 | EtOH—IPE | $C_{22}H_{27}N_2O_3F.HCl$ | 58.00<br>58.01 | 6.20<br>6.11 | 6.16<br>6.22 | A |
| 15 | 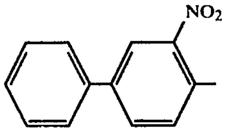 | $-O(CH_2)_3-$ | 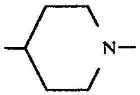 | 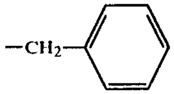 | 179~180 | EtOH | $C_{27}H_{30}N_2O_3.HCl$ | 69.44<br>69.51 | 6.69<br>6.72 | 6.06<br>6.11 | E |
| 16 | 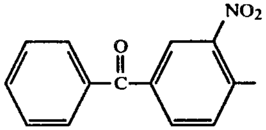 | $-O(CH_2)_3-$ | 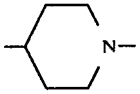 | 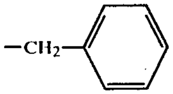 | 135~137 | Acetone IPE | $C_{25}H_{28}N_2O_2.HCl$ | 68.21<br>68.01 | 5.93<br>6.02 | 5.68<br>5.58 | E |

TABLE 1-continued $R^1$—X—Ⓐ—$R^2$

| Example | $R^1$ | X | Ⓐ | $R^2$ | Melting point (°C.) | Solvent for recrystallization | Molecular formula | Elemental analytical value (%) Upper column: Theoretical value (%) Bottom column: Found value (%) C | H | N | Preparation method |
|---|---|---|---|---|---|---|---|---|---|---|---|
| 17 | 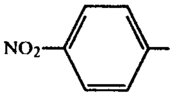 | $-OCH_2CH_2CH=$ | 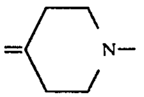 | 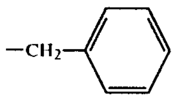 | 214~217 | EtOH—$H_2O$ | $C_{21}H_{24}N_2O_3.HCl.\frac{1}{4}H_2O$ | 64.12<br>64.12 | 6.53<br>6.58 | 7.12<br>7.24 | E |
| 18 | 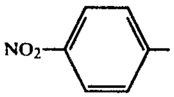 | $-O(CH_2)_7-$ | 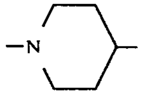 | 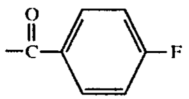 | 159~161 | EtOH—IPE | $C_{25}H_{31}N_2O_4F.HCl$ | 62.68<br>62.39 | 6.75<br>6.69 | 5.85<br>5.99 | A |
| 19 | 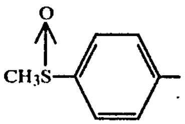 | $-CONH(CH_2)_2-$ | 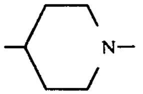 | 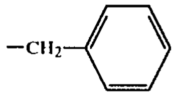 | 107~113 | EtOH<br>Ether | $C_{22}H_{28}N_2O_2S.HCl$ | 62.77<br>62.71 | 6.94<br>6.91 | 6.65<br>6.59 | B |
| 20 | 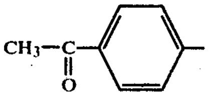 | $-CONH(CH_2)_2-$ | 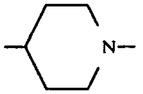 | 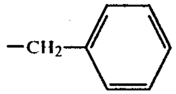 | 186~188 | EtOH<br>Ether | $C_{23}H_{30}N_2O_3.HCl$ | 66.26<br>66.15 | 7.01<br>7.18 | 6.72<br>6.61 | B |
| 21 | 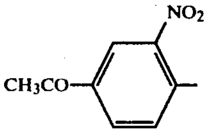 | $-CONH(CH_2)_2-$ | 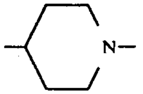 | 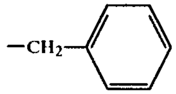 | 156~158 | — | $C_{22}H_{28}N_2O_4.HCl$ | 63.80<br>63.74 | 6.75<br>6.78 | 6.47<br>6.61 | B |
| 22 | 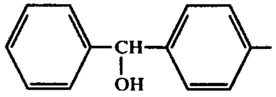 | $-CONH(CH_2)_2-$ | 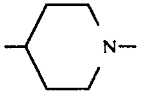 | 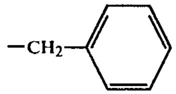 | 166~168 | — | $C_{26}H_{32}N_2O_2.HCl$ | 78.47<br>76.57<br>76.54<br>($3/5H_2O$) | 7.53<br>7.58<br>7.62 | 6.54<br>6.24<br>6.38 | B |
| 23 | 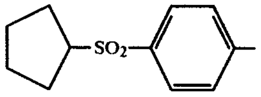 | $-CONH(CH_2)_2-$ | 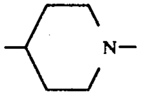 | 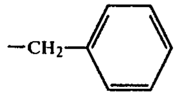 | 245~247 (Decomposition) | EtOH<br>Ether | $C_{26}H_{34}N_2O_3S.$<br>$HCl.\frac{1}{2}H_2O$ | 62.45<br>61.99 | 7.26<br>7.03 | 5.60<br>5.68 | B |

TABLE 1-continued $R^1$—X—(A)—$R^2$

| Example | $R^1$ | X | (A) | $R^2$ | Melting point (°C.) | Solvent for recrystallization | Molecular formula | Elemental analytical value (%) Upper column: Theoretical value (%) Bottom column: Found value (%) C | H | N | Preparation method |
|---|---|---|---|---|---|---|---|---|---|---|---|
| 24 | 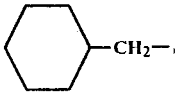 | $-CONH(CH_2)_2-$ | 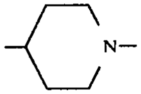 | 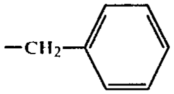 | 182~184 | EtOH | $C_{23}H_{26}N_2O_2.HCl$ | 68.29<br>68.33 | 7.03<br>7.16 | 7.24<br>7.41 | B |
| 25 | 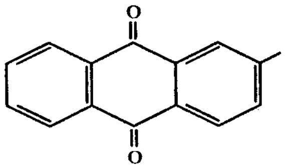 | $-CONH(CH_2)_2-$ | 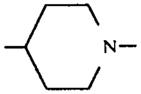 | 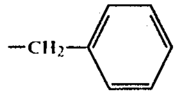 | 255~257 (Decomposition) | EtOH | $C_{21}H_{28}N_2O_3.HCl$ | 71.23<br>71.51 | 5.98<br>5.80 | 5.73<br>5.81 | B |
| 26 | 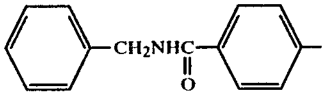 | $-CONH(CH_2)_2-$ | 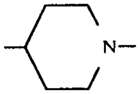 | 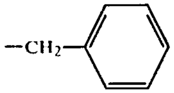 | 225~226 | EtOH | $C_{27}H_{33}N_2O_2.HCl$ | 70.79<br>70.91 | 6.96<br>7.03 | 8.54<br>8.61 | B |
| 27 | 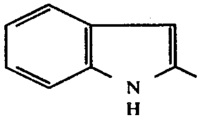 | $-CONH(CH_2)_2-$ | 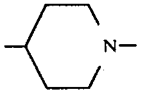 | 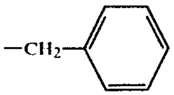 | 234~235 | EtOH<br>Ether | $C_{23}H_{27}N_3O.HCl$ | 69.42<br>69.31 | 7.09<br>7.00 | 10.56<br>10.46 | B |
| 28 | 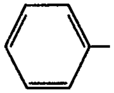 | $CH_3$<br>$-CON(CH_2)_2-$ | 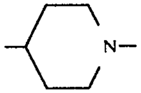 | 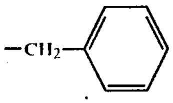 | 183-184 | — | $C_{22}H_{28}N_2O.HCl$ | 70.85<br>70.87 | 7.84<br>7.75 | 7.51<br>7.54 | B |
| 29 | 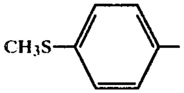 | $CH_3$<br>$-CON(CH_2)_2-$ | 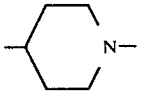 | 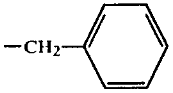 | 174~175 | — | $C_{23}H_{30}N_2OS.HCl$ | 65.93<br>65.98 | 7.46<br>7.44 | 6.69<br>6.65 | B |

TABLE 1-continued $R^1-X-$Ⓐ$-R^2$

| Example | $R^1$ | X | Ⓐ | $R^2$ | Melting point (°C.) | Solvent for recrystallization | Molecular formula | Elemental analytical value (%) Upper column: Theoretical value (%) Bottom column: Found value (%) C | H | N | Preparation method |
|---|---|---|---|---|---|---|---|---|---|---|---|
| 30 | 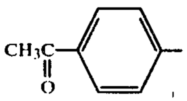 | 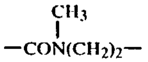 | 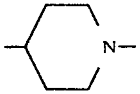 | 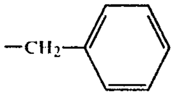 | 164~165 | — | $C_{24}H_{30}N_2O_2.HCl$ | 69.47<br>69.34 | 7.53<br>7.53 | 6.75<br>6.68 | B |
| 31 | 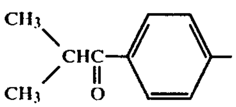 | 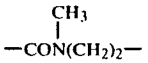 | 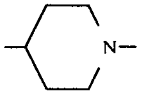 | 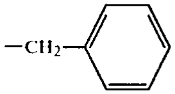 | 185~186 | — | $C_{26}H_{34}N_2O_2.HCl$ | 70.49<br>70.18 | 7.96<br>7.83 | 6.32<br>6.54 | B |
| 32 | 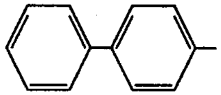 | 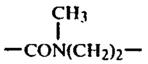 | 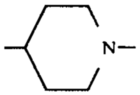 | 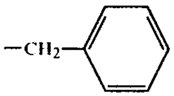 | 195~196 | — | $C_{28}H_{32}N_2O.HCl$ | 74.90<br>74.60 | 7.41<br>7.46 | 6.24<br>6.28 | B |
| 33 | 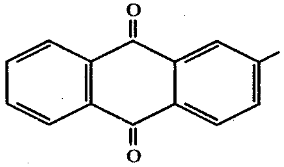 | 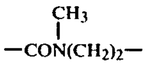 | 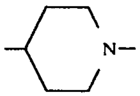 | 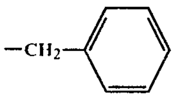 | 235~236 | EtOH | $C_{30}H_{36}N_2O_3.HCl.\frac{1}{2}H_2O$ | 70.37<br>70.12 | 6.30<br>6.23 | 5.47<br>5.28 | B |
| 34 | 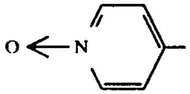 | $-CONH(CH_2)_2-$ | 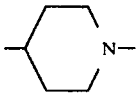 | 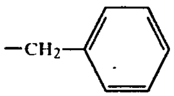 | 119~123 | EtOH<br>IPE | $C_{20}H_{23}N_3O_2.HCl$ | 63.91<br>63.88 | 6.97<br>6.98 | 11.18<br>11.16 | B |
| 35 | 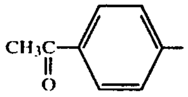 | 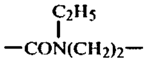 | 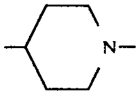 | 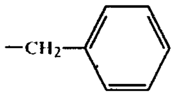 | 203~204 | — | $C_{23}H_{32}N_2O_2.HCl$ | 70.00<br>70.00 | 7.75<br>7.80 | 6.53<br>6.47 | B |
| 36 | 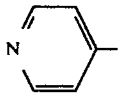 | $-CONH(CH_2)_2-$ | 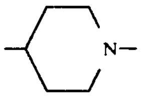 | $-CH_3$ | 161~164 | — | $C_{14}H_{21}N_3O$ | 67.98<br>67.91 | 8.56<br>8.48 | 16.99<br>16.76 | B |

TABLE 1-continued $R^1$—X—(A)—$R^2$

| Example | $R^1$ | X | (A) | $R^2$ | Melting point (°C.) | Solvent for recrystallization | Molecular formula | Elemental analytical value (%) Upper column: Theoretical value (%) Bottom column: Found value (%) C | H | N | Preparation method |
|---|---|---|---|---|---|---|---|---|---|---|---|
| 37 | 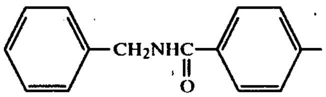 | —CONH(CH2)2— | 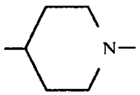 | 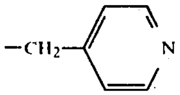 | 106~110 | MeOH<br>Ether | $C_{28}H_{32}N_4O_2.2HCl$ | 63.51<br>63.35 | 6.47<br>6.59 | 10.58<br>10.66 | B |
| 38 | 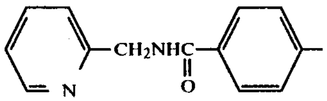 | —CONH(CH2)2— | 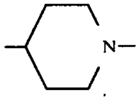 | 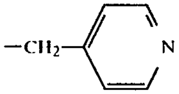 | 127~129 | MeOH<br>IPE | $C_{28}H_{31}N_3O_2.3HCl$ | 58.09<br>58.18 | 5.92<br>5.99 | 12.09<br>11.81 | B |
| 39 | 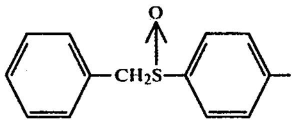 | —CONH(CH2)2— | 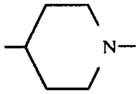 | 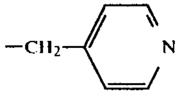 | 118~122 | Acetone<br>IPE | $C_{27}H_{31}N_3O_2S.2HCl$ | 60.66<br>60.88 | 6.22<br>6.01 | 7.86<br>7.59 | B |
| 40 | 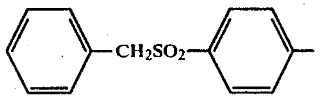 | 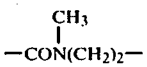 | 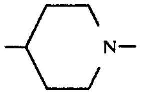 | 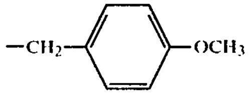 | 135~136 | Acetone<br>n-Hexane | $C_{30}H_{34}N_2O_4S$ | 69.20<br>68.89 | 6.97<br>6.87 | 5.38<br>5.09 | B |
| 41 | 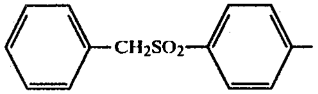 | 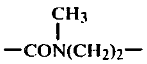 | 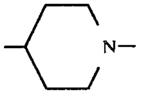 | 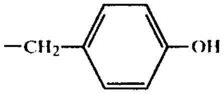 | 176~178 | — | $C_{29}H_{34}N_2O_4S$ | 68.75<br>68.66 | 6.76<br>6.68 | 5.53<br>5.27 | B |
| 42 | 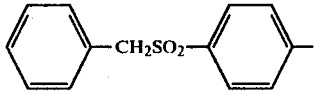 | 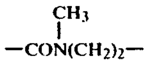 | 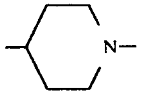 | —H | 149~151 | MeOH<br>IPE | $C_{22}H_{28}N_2O_3S$ | 65.97<br>65.92 | 7.05<br>6.95 | 6.99<br>6.90 | B |
| 43 | 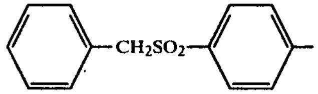 | 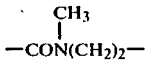 | 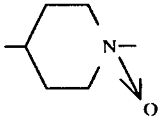 | 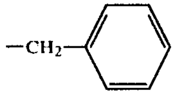 | 163~164 | EtOH<br>IPE | $C_{29}H_{34}N_2O_4S$ | 68.75<br>68.46 | 6.76<br>6.78 | 5.53<br>5.27 | B |

TABLE 1-continued $R^1-X-$Ⓐ$-R^2$

| Example | $R^1$ | X | Ⓐ | $R^2$ | Melting point (°C.) | Solvent for recrystallization | Molecular formula | Elemental analytical value (%) Upper column: Theoretical value (%) Bottom column: Found value (%) C | H | N | Preparation method |
|---|---|---|---|---|---|---|---|---|---|---|---|
| 44 | 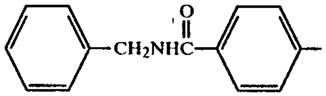 | $-\overset{CH_3}{\overset{\vert}{CON}}(CH_2)_2-$ | 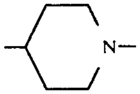 | $-CH_2CH_2OH$ | 114~116 | MeOH<br>IPE | $C_{30}H_{31}N_3O_3.HCl$ | 69.55<br>69.49 | 6.23<br>6.33 | 8.11<br>8.19 | B |
| 45 | 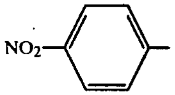 | $-SO_2NH(CH_2)_2-$ | 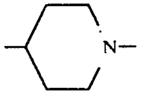 | 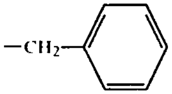 | 122~123 | EtOH | $C_{16}H_{25}N_3O_4S$ | 61.68<br>61.57 | 6.47<br>6.33 | 7.19<br>7.02 | B |
| 46 | 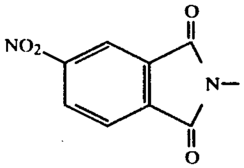 | — | 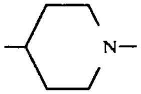 | 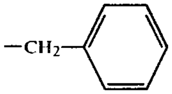 | 254~255 | EtOH | $C_{20}H_{17}N_3O_4.HCl$ | 59.78<br>59.99 | 5.02<br>5.13 | 10.46<br>10.41 | C |
| 47 | 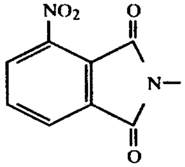 | $-(CH_2)_2-$ | 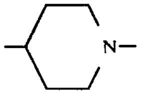 | 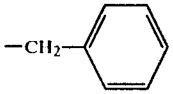 | 177~179 | EtOH<br>Ether | $C_{22}H_{23}N_3O_4.HCl$ | 61.47<br>61.59 | 5.63<br>5.66 | 9.77<br>9.51 | C |
| 48 | 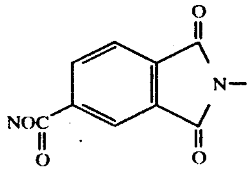 | $-(CH_2)_2-$ | 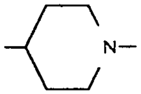 | 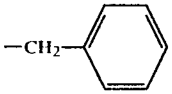 | 116~118 | MeOH<br>IPE | $C_{23}H_{28}N_2O_4.HCl$ | 61.47<br>61.30 | 5.63<br>5.61 | 9.77<br>9.87 | C |

TABLE 1-continued $R^1$—X—(A)—$R^2$

| Example | $R^1$ | X | (A) | $R^2$ | Melting point (°C.) | Solvent for recrystallization | Molecular formula | Elemental analytical value (%) Upper column: Theoretical value (%) Bottom column: Found value (%) C | H | N | Preparation method |
|---|---|---|---|---|---|---|---|---|---|---|---|
| 49 | 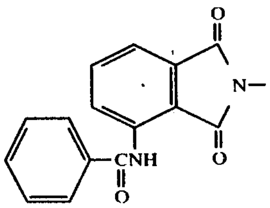 | $-(CH_2)_2-$ | 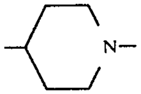 | 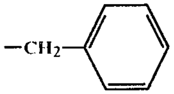 | 246~248 (Decomposition) | EtOH Ether | $C_{29}H_{27}N_3O_2.HCl$ | 69.11<br>68.96 | 6.00<br>6.12 | 8.34<br>8.39 | C |
| 50 | 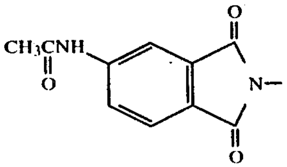 | $-(CH_2)_2-$ | 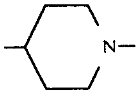 | 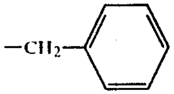 | 238~239 (Decomposition) | MeOH Ether | $C_{24}H_{27}N_3O_3.HCl$ | 65.22<br>65.43 | 6.39<br>6.28 | 9.51<br>9.60 | C |
| 51 | 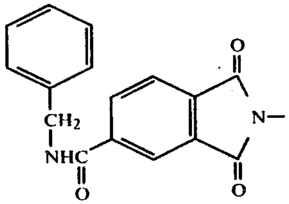 | $-(CH_2)_2-$ | 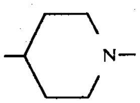 | 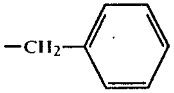 | 227~228 (Decomposition) | EtOH Ether | $C_{30}H_{31}N_3O_2.HCl$ | 69.55<br>69.29 | 6.23<br>6.34 | 8.11<br>8.08 | C |
| 52 | 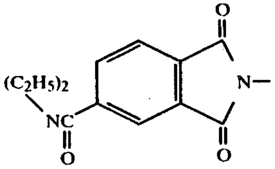 | $-(CH_2)_2-$ | 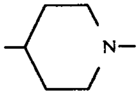 | 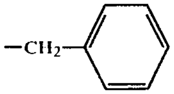 | 161~164 | EtOH Ether | $C_{27}H_{33}N_3O_3.HCl$ | 66.80<br>66.85 | 7.27<br>7.05 | 8.66<br>8.64 | C |

TABLE 1-continued $R^1$—X—Ⓐ—$R^2$

| Example | $R^1$ | X | Ⓐ | $R^2$ | Melting point (°C.) | Solvent for recrystallization | Molecular formula | Elemental analytical value (%) Upper column: Theoretical value (%) Bottom column: Found value (%) C | H | N | Preparation method |
|---|---|---|---|---|---|---|---|---|---|---|---|
| 53 | 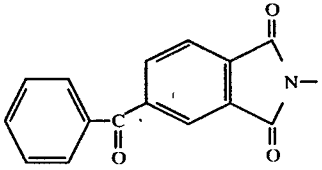 | $-(CH_2)_2-$ | 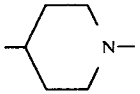 | 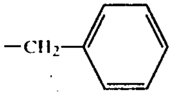 | 162 ~ 163 | -- | $C_{29}H_{28}N_2O_3.HCl$ | 71.22<br>70.98 | 5.98<br>5.96 | 5.73<br>5.79 | C |
| 54 | 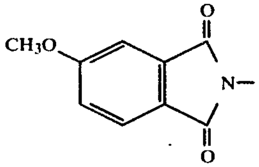 | $-(CH_2)_2-$ | 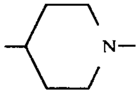 | 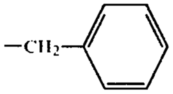 | 221 ~ 222 (Decomposition) | EtOH IPE | $C_{23}H_{24}N_2O_3.HCl$ | 66.57<br>66.42 | 6.56<br>6.59 | 6.75<br>6.67 | C |
| 55 | 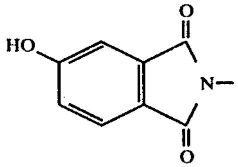 | $-(CH_2)_2-$ | 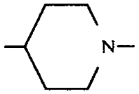 | 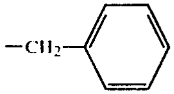 | 221 ~ 224 (Decomposition) | EtOH IPE | $C_{22}H_{24}N_2O_3.HCl$ | 65.91<br>65.77 | 6.29<br>6.34 | 6.99<br>6.69 | C |
| 56 | 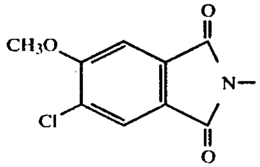 | $-(CH_2)_2-$ | 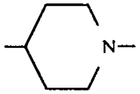 | 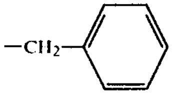 | 222 ~ 223 (Decomposition) | EtOH IPE | $C_{22}H_{23}N_2O_3Cl.HCl$ | 61.47<br>61.33 | 5.83<br>5.92 | 6.24<br>6.31 | C |
| 57 | 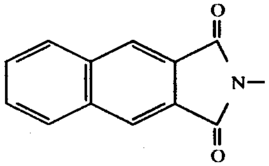 | $-(CH_2)_2-$ | 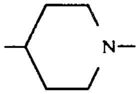 | 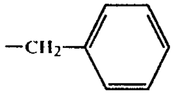 | 235 ~ 236 (Decomposition) | EtOH | $C_{24}H_{24}N_2O_2.HCl$ | 71.80<br>71.49 | 6.26<br>6.17 | 6.44<br>6.41 | C |

TABLE 1-continued $R^1$—X—Ⓐ—$R^2$

| Example | $R^1$ | X | Ⓐ | $R^2$ | Melting point (°C.) | Solvent for recrystallization | Molecular formula | Elemental analytical value (%) Upper column: Theoretical value (%) Bottom column: Found value (%) C | H | N | Preparation method |
|---|---|---|---|---|---|---|---|---|---|---|---|
| 58 | 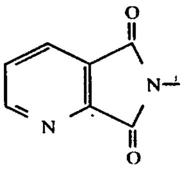 | $-(CH_2)_2-$ | 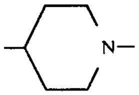 | 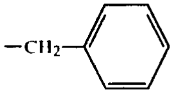 | 178~181 | Acetone IPE | $C_{21}H_{23}N_3O_2.2HCl$ | 61.77<br>61.46 | 6.17<br>6.35 | 6.86<br>7.17 | C |
| 59 | 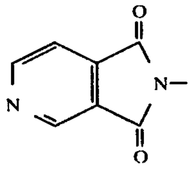 | $-(CH_2)_2-$ | 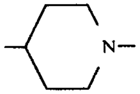 | 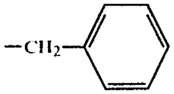 | 161~163 | Acetone IPE | $C_{21}H_{23}N_3O_2.2HCl$ | 61.77<br>61.51 | 6.17<br>6.22 | 6.86<br>7.21 | C |
| 60 | 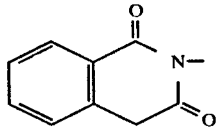 | $-(CH_2)_2-$ | 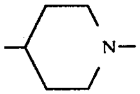 | 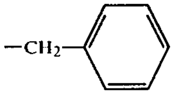 | 210~214 (Decomposition) | EtOH IPE | $C_{23}H_{24}N_2O_2.HCl$ | 69.25<br>68.96 | 6.82<br>6.80 | 7.02<br>7.02 | C |
| 61 | 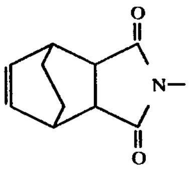 | $-(CH_2)_2-$ | 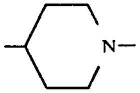 | 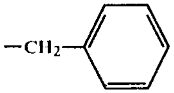 | 266~268 | EtOH MeOH | $C_{24}H_{30}N_2O_2.HCl$ | 69.47<br>69.31 | 7.53<br>7.46 | 6.72<br>6.63 | C |
| 62 | 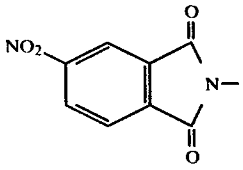 | $-(CH_2)_2-$ | 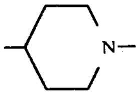 | 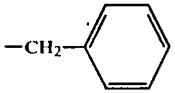 | 198~204 (Decomposition) | $CHCl_3$ Ether | $C_{23}H_{25}N_3O_4.HCl$ | 62.23<br>61.94 | 5.90<br>5.95 | 9.47<br>9.15 | C |

TABLE 1-continued

R[1]—X—(A)—R[2]

| Example | $R^1$ | X | (A) | $R^2$ | Melting point (°C.) | Solvent for recrystallization | Molecular formula | Elemental analytical value (%) Upper column: Theoretical value (%) Bottom column: Found value (%) C | H | N | Preparation method |
|---|---|---|---|---|---|---|---|---|---|---|---|
| 63 | 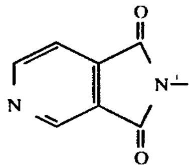 | $-(CH_2)_2-$ | 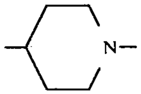 | 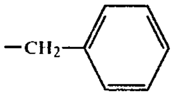 | 184~188 (Decomposition) | EtOH Ether | $C_{22}H_{25}N_3O_2.2HCl$ | 60.55<br>60.21 | 6.24<br>6.11 | 9.63<br>9.57 | C |
| 64 | 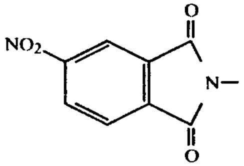 | $-(CH_2)_2-$ | 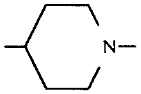 | $-CH_3$ | 256~258 (Decomposition) | EtOH IPE | $C_{16}H_{19}N_3O_4.HCl$ | 54.31<br>54.29 | 5.70<br>5.71 | 11.88<br>11.81 | C |
| 65 | 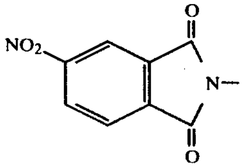 | $-(CH_2)_2-$ | 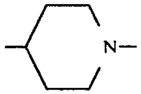 | 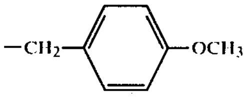 | 205~206 | — | $C_{23}H_{25}N_3O_3.HCl$ | 60.06<br>60.09 | 5.76<br>5.73 | 9.14<br>9.08 | C |
| 66 | 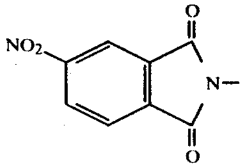 | $-(CH_2)_2-$ | 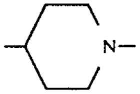 | 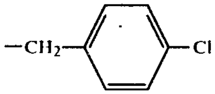 | 229~231 | — | $C_{22}H_{22}N_3O_4Cl.HCl$ | 56.91<br>56.91 | 4.99<br>5.02 | 9.05<br>9.03 | C |
| 67 | 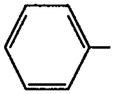 | $-CH_2NH(CH_2)_2-$ | 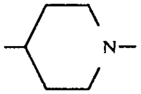 | 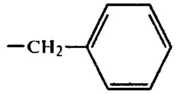 | 273~276 (Decomposition) | EtOH Ether | $C_{21}H_{20}N_2.2HCl$ | 66.14<br>65.73 | 7.93<br>7.79 | 7.35<br>7.28 | A |

TABLE 1-continued
$R^1$—X—Ⓐ—$R^2$
| Example | $R^1$ | X | Ⓐ | $R^2$ | Melting point (°C.) | Solvent for recrystallization | Molecular formula | Elemental analytical value (%) Upper column: Theoretical value (%) Bottom column: Found value (%) C | H | N | Preparation method |
|---|---|---|---|---|---|---|---|---|---|---|---|
| 68 | 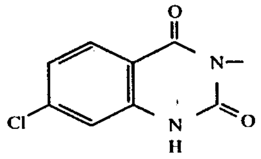 | $-(CH_2)_2-$ | 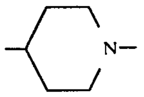 | 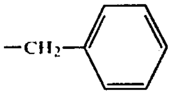 | 212~213 | EtOH | $C_{22}H_{24}N_3O_2Cl.HCl$ | 60.83<br>60.61 | 5.80<br>5.93 | 9.67<br>9.76 | D |
| 69 | 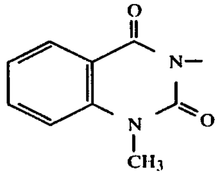 | $-(CH_2)_2-$ | 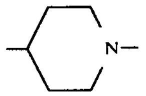 | 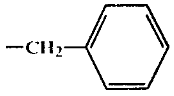 | 221~223 | EtOH<br>Ether | $C_{23}H_{27}N_3O_2.HCl$ | 66.74<br>66.92 | 6.82<br>6.71 | 10.15<br>10.04 | D |

TABLE 2
$R^1-X-$Ⓐ$-R^2$
| Example | $R^1$ | X | Ⓐ |
|---|---|---|---|
| 70 | 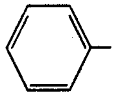 | $-CONH(CH_2)_2-$ | 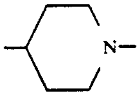 |
| 71 | 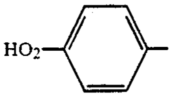 | $-CONH(CH_2)_2-$ | 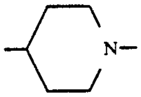 |
| 72 | 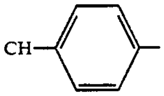 | $-CONH(CH_2)_2-$ | 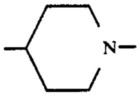 |
| 73 | 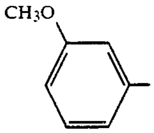 | $-CONH(CH_2)_2-$ | 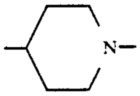 |
| 74 | 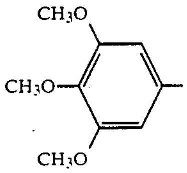 | $-CONH(CH_2)_2-$ | 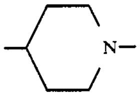 |
| 75 | 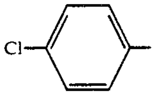 | $-CONH(CH_2)_2-$ | 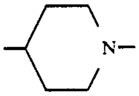 |
| 76 | 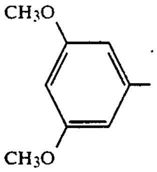 | $-CONH(CH_2)_2-$ | 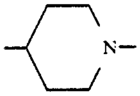 |
| 77 | 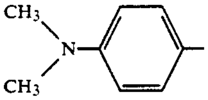 | $-CONH(CH_2)_2-$ | 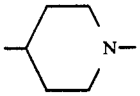 |
| 78 | 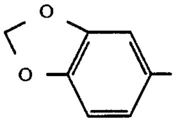 | $-CONH(CH_2)_2-$ | 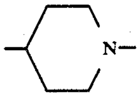 |
| 79 | 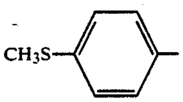 | $-CONH(CH_2)_2-$ | 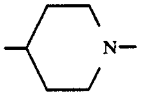 |
| 80 | 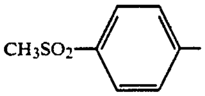 | $-CONH(CH_2)_2-$ | 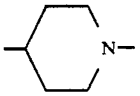 |

TABLE 2-continued
| $R^1$—X—Ⓐ—$R^2$ | | | |
|---|---|---|---|
| 81 | 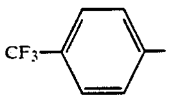 | —CONH$(CH_2)_2$— | 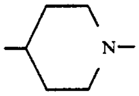 |
| 82 | 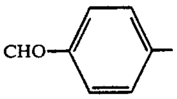 | —CONH$(CH_2)_2$— | 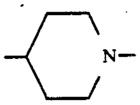 |
| 83 | 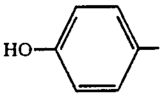 | —CONH$(CH_2)_2$— | 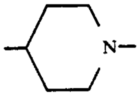 |
| 84 | 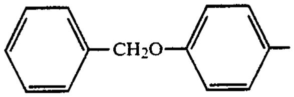 | —CONH$(CH_2)_2$— | 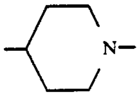 |
| 85 | 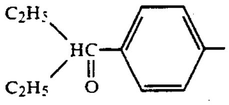 | —CONH$(CH_2)_2$— | 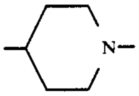 |
| 86 | 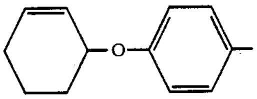 | —CONH$(CH_2)_2$— | 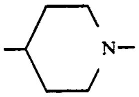 |
| 87 | 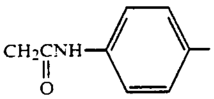 | —CONH$(CH_2)_2$— | 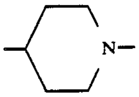 |
| 88 | 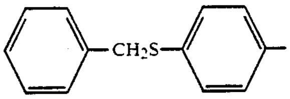 | —CONH$(CH_2)_2$— | 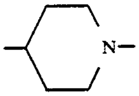 |
| 89 | 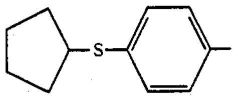 | —CONH$(CH_2)_2$— | 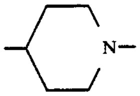 |
| 90 | 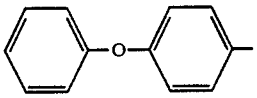 | —CONH$(CH_2)_2$— | 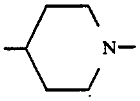 |
| 91 | 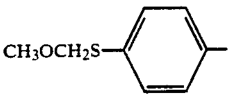 | —CONH$(CH_2)_2$— | 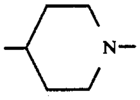 |
| 92 | 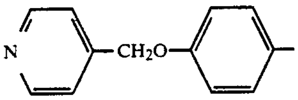 | —CONH$(CH_2)_2$— | 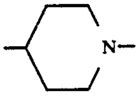 |
| 93 | 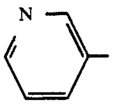 | —CONH$(CH_2)_2$— | 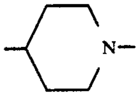 |

TABLE 2-continued
$R^1-X-(A)-R^2$
| | | | |
|---|---|---|---|
| 94 | 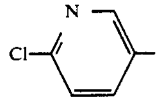 | $-CONH(CH_2)_2-$ | 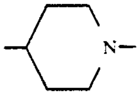 |
| 95 | 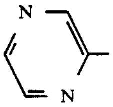 | $-CONH(CH_2)_2-$ | 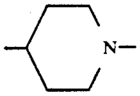 |
| 96 | 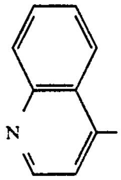 | $-CONH(CH_2)_2-$ | 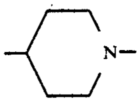 |
| 97 | 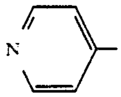 | $-CONHCH_2CH-$ | 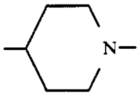 |
| 98 | 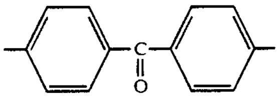 | $CH_3$<br>$-CON(CH_2)_2-$ | 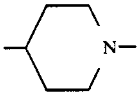 |
| 99 | 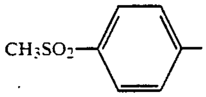 | $CH_3$<br>$-CON(CH_2)_2-$ | 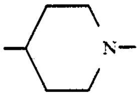 |
| 100 | 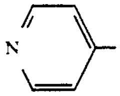 | $C_2H_5$<br>$-CON(CH_2)_2-$ | 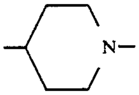 |
| 101 | 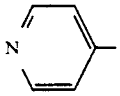 | 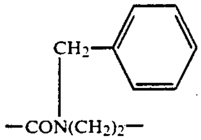 | 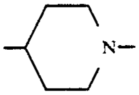 |
| 102 | 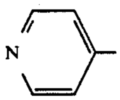 | $-CONH(CH_2)_2-$ | 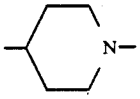 |
| 103 | 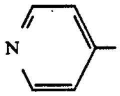 | $-CONH(CH_2)_2-$ | 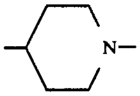 |
| 104 | 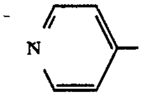 | $-CONH(CH_2)_2-$ | 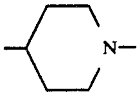 |
| 105 | 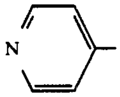 | $-CONH(CH_2)_2-$ | 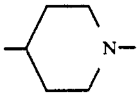 |

TABLE 2-continued
| | $R^1$—X—Ⓐ—$R^2$ | | |
|---|---|---|---|
| 106 | 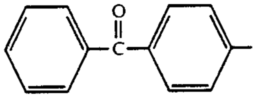 | $-CONH(CH_2)_2-$ | 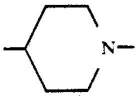 |
| 107 | 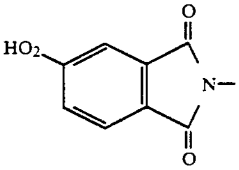 | $-CH_3-$ | 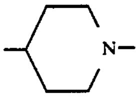 |
| 108 | 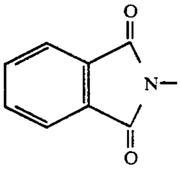 | $-(CH_2)_2-$ | 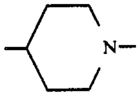 |
| 109 | 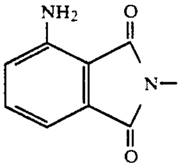 | $-(CH_2)_2-$ | 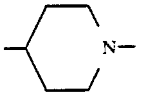 |
| 110 | 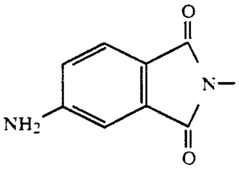 | $-(CH_2)_2-$ | 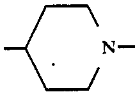 |
| 111 | 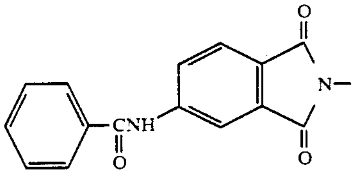 | $-(CH_2)_2-$ | 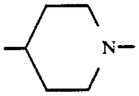 |
| 112 | 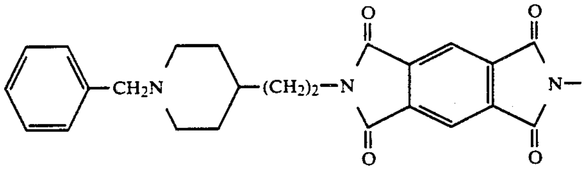 | $-(CH_2)_2-$ | 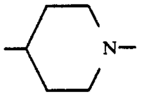 |
| 113 | 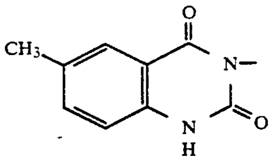 | $-(CH_2)_2-$ | 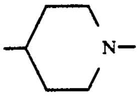 |
| 114 | 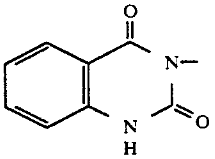 | $-(CH_2)_2-$ | 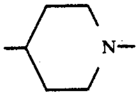 |

TABLE 2-continued
$R^1$—X—Ⓐ—$R^2$
| | | | |
|---|---|---|---|
| 115 | 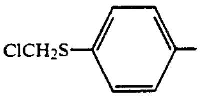 | $-CONH(CH_2)_2-$ | 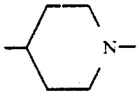 |
| 116 | 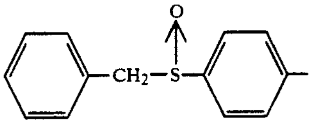 | $-CONH(CH_2)_2-$ | 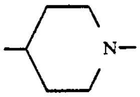 |
| 117 | 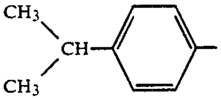 | $-CONH(CH_2)_2-$ | 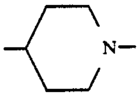 |
| 118 | 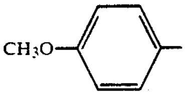 | $-CONH(CH_2)_2-$ | 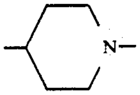 |
| 119 | 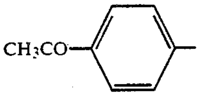 | $-CONH(CH_2)_2-$ | 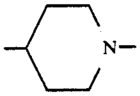 |
| 120 | 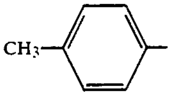 | $-CONH(CH_2)_2-$ | 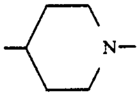 |
| 121 | 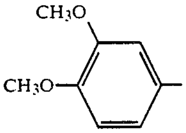 | $-CONH(CH_2)_2-$ | 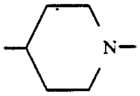 |
| 122 | 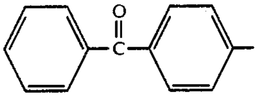 | $-CONH(CH_2)_2-$ | 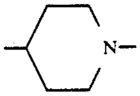 |
| 123 | 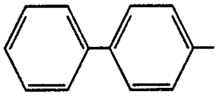 | $-CONH(CH_2)_2-$ | 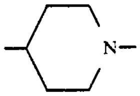 |
| 124 | 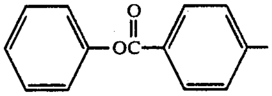 | $-CONH(CH_2)_2-$ | 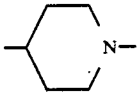 |
| 125 | 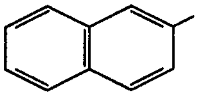 | $-CONH(CH_2)_2-$ | 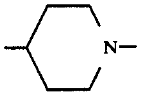 |
| 126 | 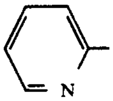 | $-CONH(CH_2)_2-$ | 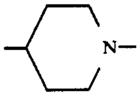 |
| 127 | 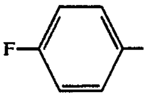 | $-CONH(CH_2)_2-$ | 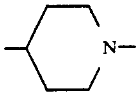 |

TABLE 2-continued
| $R^1-X-(A)-R^2$ | | | |
|---|---|---|---|
| 128 | 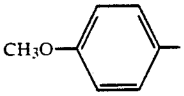 | $CH_3$<br>$-CON(CH_2)_2-$ | 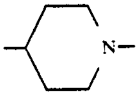 |
| 129 | 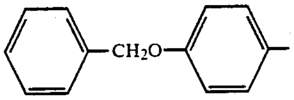 | $CH_3$<br>$-CON(CH_2)_2-$ | 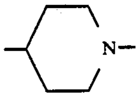 |
| 130 | 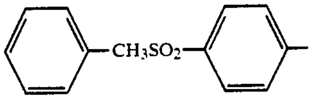 | $C_2H_5$<br>$-CON(CH_2)_2-$ | 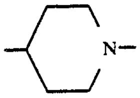 |
| 131 | 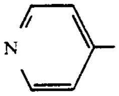 | $-CONHCH_2-$ | 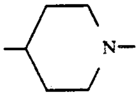 |
| 132 | 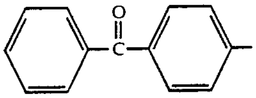 | $-CONH(CH_2)_2-$ | 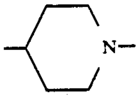 |
| 133 | 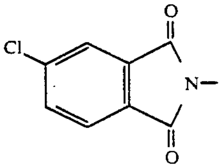 | $-(CH_2)_2-$ | 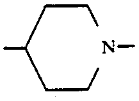 |
| 134 | 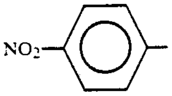 | $-CON-(CH_2)_2-$<br>$CH_3$ | 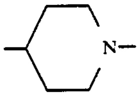 |
| 135 | 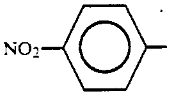 | $-CON-(CH_2)_2-$<br>$CH_2CH_3$ | 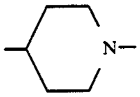 |
| 136 | 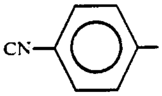 | $-CON-(CH_2)_2-$<br>$CH_3$ | 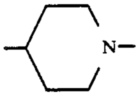 |
| 137 | 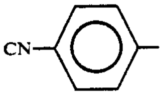 | $-CON-(CH_2)_2-$<br>$CH_2CH_3$ | 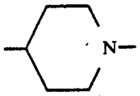 |
| Example | $R^2$ | Molecular formula | $H^1$-NMR($CDCl_3$, ppm) | Preparation method |
|---|---|---|---|---|
| 70 | 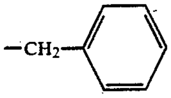 | $C_{21}H_{26}H_7O.HCl$ | 1.16~2.04(9H, m), 2.7~2.96(2H, d), 3.28~3.56(4H, m), 6.0(1H, s), 7.2~7.76(10H, m) | B |
| 71 | 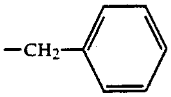 | $C_{21}H_{25}N_3O_2$ | 1.08~2.12(9H, m), 2.84~2.96(2H, d), 3.38~3.6(2H, m), 3.52(2H, s), 6.40(1H, bt), 7.3(5H, s), 7.9 (2H, d), 8.24(2H, d) | B |

TABLE 2-continued $R^1$—X—Ⓐ—$R^2$

| | | | | |
|---|---|---|---|---|
| 72 | 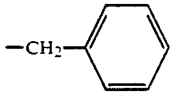 | $C_{21}H_{23}N_3O$ | 1.1~2.06(9H, m), 2.8~2.9(2H, bd), 3.32~3.56(4H, sim), 6.36 (1H, t), 7.26(5H, s), 7.64(2H, d), 7.84(2H, d) | B |
| 73 | 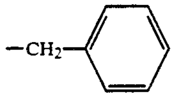 | $C_{22}H_{28}N_2O_2$ | 1.24~2.03(9H, m), 2.8~2.86(2H, d), 3.26~3.48(2H, m), 3.46(2H, s), 3.8(3H, s), 6.14(1H, bt), 6.9~7.3(9H, m) | B |
| 74 | 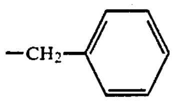 | $C_{24}H_{31}N_2O_4$ | 1.23~2.04(9H, m), 2.76~2.88(2H, bd), 3.35~3.58(4H, sit), 3.84 (9H, s), 6.38(1H, bt), 7.0(2H, s), 7.28(5H, s) | B |
| 75 | 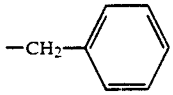 | $C_{21}H_{25}N_2OCl$ | 2.9(2H, d), 3.45(3H, s, d), 6.26 (1H, bt), 7.26(5H, s), 7.3(2H, d), 7.7(2H, d) | B |
| 76 | 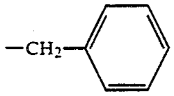 | $C_{23}H_{34}N_2O_4$ | 2.9(2H, d), 3.46(3H, s, d), 3.78 (6H, s), 6.12(1H, bt), 6.5(1H, t), 6.82(2H, d), 7.26(5H, s) | B |
| 77 | 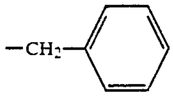 | $C_{23}H_{31}N_3O$ | 2.7(2H, d), 2.8(6H, s), 3.34(2H, s), 6.46(2H, d), 6.5(1H), 7.12 (5H, s), 7.59(2H, d) | B |
| 78 | 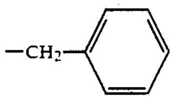 | $C_{22}H_{26}H_2O_3$ | 1.1~2.0(9H, m), 2.76~2.86(2H, bd), 3.26~3.48(4H, m), 5.94(2H, s), 6.32(1H, bt), 6.72(1H, d), 7.24(2H, s) | B |
| 79 | 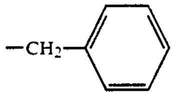 | $C_{23}H_{28}N_2OS$ | 1.02~2.04(9H, m), 2.8~2.9(2H, bd), 2.8~2.9(2H, bd), 3.2~3.5 (4H, sim), 6.26(1H, bt), 7.18(2H, d), 7.28(5H, s), 7.64(2H, d) | B |
| 80 | 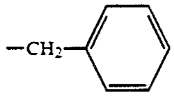 | $C_{22}H_{28}N_2O_3S$ | 1.12~2.06(9H, m), 2.8~2.9(2H, bd), 3.04(3H, s), 3.36~3.58(2H, m), 3.48(2H, s), 6.3(1H, bt), 7.26 (5H, s), 7.9(4H, s) | B |
| 81 | 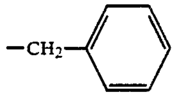 | $C_{21}H_{23}N_3OF_2$ | 1.3~2.08(9H, m), 2.86(2H, bd), 3.46(2H, s), 6.0(1H, bs), 7.16(5H, s), 7.64(2H, d), 7.82(2H, d) | B |
| 82 | 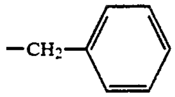 | $C_{23}H_{26}N_2O_2$ | 1.2~2.20(9H, m), 2.98(2H, bd), 3.42(3H, m), 3.60(2H, s), 7.30(5H, s), 7.92(4H, s), 10.02(1H, s) | B |
| 83 | 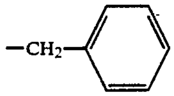 | $C_{21}H_{26}N_2O_2$ | 1.2~2.04(9H, m), 2.84(2H, bd), 3.30(2H, m), 3.46(2H, s), 6.52(1H, bs), 6.66(2H, d), 7.22(5H, s), 7.52(2H, d), 8.30(1H, s) | B |
| 84 | 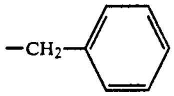 | $C_{26}H_{31}N_2O_2$ | 1.1~2.04(9H, m), 2.84(2H, bd), 3.44(4H, sim), 5.06(2H, m), 6.00 (1H, bt), 6.92(2H, d), 7.14~7.44 (10H, m), 7.68(2H, d) | B |

TABLE 2-continued $R^1$—X—Ⓐ—$R^2$

| | | | | |
|---|---|---|---|---|
| 85 | 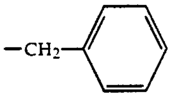 | $C_{26}H_{33}N_2O_2$ | 1.06~2.04(15H, m), 2.8(2H, bd), 3.10~3.60(8H, sim), 6.96(1H, bt), 7.22(7H, sid), 7.66(2H, d) | B |
| 86 | 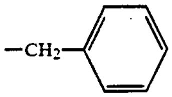 | $C_{27}H_{34}N_2O_2$ | 1.1~2.1(15H, m), 2.76~2.88(2H, bd), 3.3~3.5(2H, m), 3.44(2H, s), 4.8(1H, m), 5.7~6.04(2H, m), 6.88 (2H, d), 7.28(5H, m), 7.64(2H, d) | B |
| 87 | 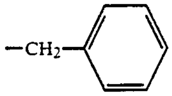 | $C_{23}H_{25}N_3O_2$ | 1.3~2.0(7H, m), 2.7~3.4(6H, m), 4.14~4.36(5H, m), 7.3~8.04(9H, m), 8.40(1H, m), 10.00(1H, m) | B |
| 88 | 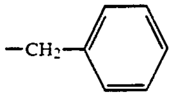 | $C_{28}H_{31}N_2OS$ | 1.0~1.98(9H, m), 2.6~2.86(2H, m), 3.08~3.5( , mis), 4.28(2H, s), 7.2~7.4(12H, m), 7.7(2H, d), 8.32(1H, bt) | B |
| 89 | 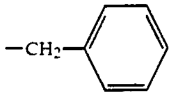 | $C_{26}H_{34}N_2OS$ | 1.2~2.3(17H, m), 3.08~3.2(2H, bd), 2.5~2.78(5H, m), 3.1(1H, m), 7.06~7.9(9H, m) | B |
| 90 | 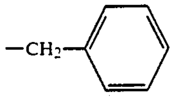 | $C_{27}H_{30}N_2O_2$ | 1.24~2.04(9H, m), 2.76~2.88(2H, bd), 3.3~3.5(6H, sim), 6.1(1H, bt), 6.88~7.74(14H, m) | B |
| 91 | 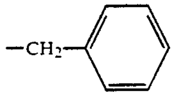 | $C_{32}H_{30}N_2O_2S$ | 1.22~2.06(9H, m), 2.8~2.92(2H, bd), 3.38(3H, s), 3.44(2H, s), 3.28~3.44(2H, m), 4.94(2H, s), 6.36(1H, bt), 7.26(5H, s), 7.4(2H, d), 7.65(2H, d) | B |
| 92 | 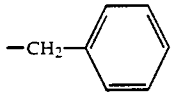 | $C_{27}H_{31}N_3O_2$ | 1.24~2.06(9H, m), 2.88(2H, bd), 3.40(2H, t), 3.48(2H, s), 5.11(2H, s), 5.94(1H, bs), 6.94(2H, d), 7.28(5H, s), 7.32(2H, d), 7.7(2H, d), 8.6(2H, d) | B |
| 93 | 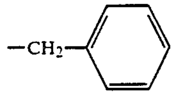 | $C_{20}H_{25}N_2O$ | 2.9(2H, d), 3.48(3H, s, d), 6.7(1H, bt), 7.28(6H, s), 7.1(1H, ), 7.65 (1H, ), 7.9(1H, ) | B |
| 94 | 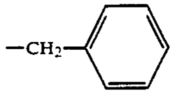 | $C_{20}H_{24}N_3OCl$ | 1.26~2.05(9H, m), 2.8~2.9(2H, bd), 3.32~3.54(4H, sim), 6.56 (1H, bt), 7.28(5H, s), 7.34(1H, d), 8.02(1H, dd), 8.7(1H, d) | B |
| 95 | 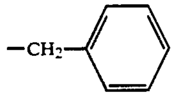 | $C_{17}H_{24}N_4O$ | 1.3~2.07(9H, m), 2.8~2.92(2H, bd), 2.38~2.6(4H, sim), 7.27 (5H, s), 7.7(1H, bt), 8.5(1H, g), 8.7(1H, d), 9.38(1H, d) | B |
| 96 | 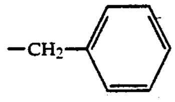 | $C_{24}H_{26}N_3O$ | 2.86(2H, d), 3.48(4H, s, d), 6.44 (1H, lb), 7.26(5H, s), 7.4~7.8 (3H), 8.4(2H), 8.74(1H, d) | B |
| 97 | 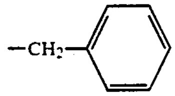 | $C_{20}H_{23}N_3O$ | 2.24~2.56(8H, m), 3.56(2H, s), 4.0(2H, t), 5.28(1H, t), 6.64(1H, bs), 7.31(5H, s), 7.6(2H, dd), 8.66(2H, dd) | B |

TABLE 2-continued $R^1—X—(A)—R^2$

| | | | | |
|---|---|---|---|---|
| 98 | 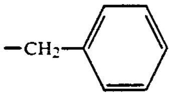 | $C_{27}H_{21}N_2O_2$.HCl | 0.8~2.10(11H, m), 2.49~2.88 (7H, m), 7.04~7.84(14H, m) | B |
| 99 | 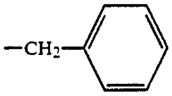 | $C_{13}H_{30}N_2O_3S$.HCl | 0.92~2.10(9H, m), 2.44~3.6(7H, m), 3.0(3H, s), 3.44(2H, bd), 7.14 (5H, s), 7.52(2H, d), 7.96(2H, d) | B |
| 100 | 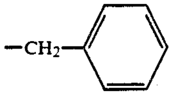 | $C_{12}H_{29}N_3O$ | 1.02~2.10(12H, m), 2.7~3.7(8H, m), 8.2~8.28(7H, d, s), 8.68(2H, d) | B |
| 101 | 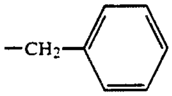 | $C_{27}H_{31}N_3O$ | 1.04~2.04(9H, m), 2.7~3.7(6H, m), 4.4(2H, s), 4.74(2H, s), 7.00~7.6(12H, m), 8.64(2H, bs) | B |
| 102 | 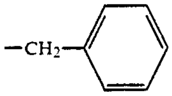 | $C_{11}H_{27}N_3O$ | 1.14~2.04(11H, m), 2.78~2.9(2H bd), 3.16~3.76(4H, s, d), 6.5 (1H, s), 7.26(5H, s), 7.56(2H, d), 8.68(2H, d) | B |
| 103 | 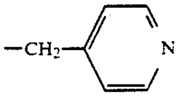 | $C_{19}H_{24}N_4O$ | 1.3~2.1(9H, m), 2.76~2.88(2H, m), 3.16~3.58(4H, m, s), 6.84(1H, s), 7.24(2H, d), 7.6(2H, d), 8.48 (2H, d), 8.68(2H, d) | B |
| 104 | 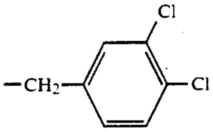 | $C_{19}H_{13}N_3O_2Cl_2$ | 2.0(2H, d), 3.4(4H, s, t), 7.5~7.1(3H), 7.62(2H), 8.64(2H) | B |
| 105 | 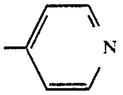 | $C_{18}H_{22}N_4O$ | 1.22~1.96(7H, m), 2.7~3.0(2H, m), 3.4~3.62(2H, m), 3.8~3.85 (2H, m), 6.62(3H, m, s), 7.58(2H, d), 8.7(2H, d) | B |
| 106 | 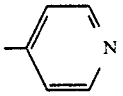 | $C_{11}H_{27}N_3O_2$ | 1.04~2.16(9H, m), 2.82(2H, d), 3.32~3.62(2H, m), 3.46(2H, s), 6.32~6.58(1H, m), 7.16~8.56 (13H, m) | B |
| 107 | 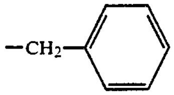 | $C_{31}H_{21}N_3O_4$ | 1.26~2.06(9H, m), 2.78~2.9(2H, bd), 3.45(2H, s), 3.62(2H, d), 7.24(5H, s), 7.95~8.04(1H, m), 8.5~8.6(2H, m) | C |
| 108 | 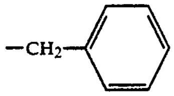 | $C_{21}H_{24}N_3O_2$ | 1.26~2.04(9H, m), 2.84(2H, bd), 3.44(2H, s), 3.68(2H, t), 7.24 (5H, s), 7.7(4H, m) | C |
| 109 | 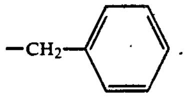 | $C_{11}H_{13}N_3O_2$ | 1.28~2.04(9H, m), 2.85(2H, bd), 3.46(2H, s), 3.62(2H, t), 5.17 (2H, s), 6.78(1H, d), 7.1(1H, d), 7.25(5H, s), 7.36(1H, t) | C |
| 110 | 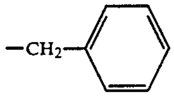 | $C_{22}H_{25}N_3O_2$ | 1.26~2.04(9H, m), 2.84(2H, bd), 3.48(2H, s), 3.6(2H, t), 5.31 (2H, s), 6.76(1H, dd), 6.98(1H, d), 7.27(5H, s), 7.54(1H, d) | C |

TABLE 2-continued

| $R^1$—X—(A)—$R^2$ | | | | |
|---|---|---|---|---|
| 111 | 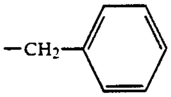 | $C_{27}H_{27}N_3O_3$ | 1.28~2.06(9H, m), 2.86(2H, bd), 3.50(2H, s), 3.68(2H, t), 7.28 (5H, s), 7.50(3H, m), 7.86(3H, m), 8.1(2H, m), 8.36(1H, s) | C |
| 112 | 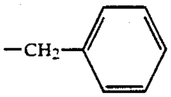 | $C_{28}H_{43}N_4O_4$ | 2.84(2H, d), 2.44(2H, s), 2.7 (2H, t), 7.24(10H, s), 8.2(2H, s) | C |
| 113 | 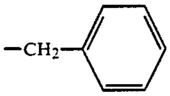 | $C_{13}H_{17}N_3O_2$ | 1.0~2.2(8H, m), 2.41(3H, s), 2.7~3.1(2H, m), 3.5(2H, s), 4.11(2H, t), 7.8~8.9(8H, m) | D |
| 114 | 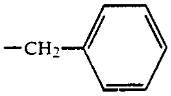 | $C_{13}H_{27}N_3O_2$ | 0.9~2.2(8H, m), 2.7~3.0(2H, m), 3.48(2H, s), 4.06(2H, t), 7.9~8.7(8H, m), 8.0~8.2 (1H, m) | D |
| 115 | 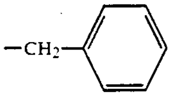 | $C_{22}H_{27}N_2OSCl.HCl.\frac{1}{2}H_2O$ | 0.92~2.04(9H, m), 2.64~3.00(2H, bd), 3.12~3.60(2H, m), 3.40(2H, s), 4.96(2H, s), 6.48~6.76(1H, bt), 7.08~7.84(9H, m) | B |
| 116 | 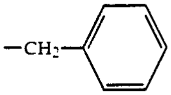 | $C_{28}H_{32}N_2O_2S.HCl.\frac{1}{2}H_2O$ | 1.0~2.10(9H, m), 2.70~2.96(2H, bd), 3.20~3.60(2H, m), 3.46(2H, s), 4.00(2H, d), 6.20 (1H, bs), 6.84~7.80(14H, m) | B |
| 117 | 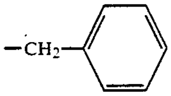 | $C_{24}H_{27}N_2O.HCl$ | 1.20(3H, s), 1.28(3H, s), 1.00~2.08(9H, m), 2.64~3.02(3H, m), 3.45(2H, s), 3.24~3.56 (2H, m), 6.36(1H, bt), 7.12~7.76(9H, m) | B |
| 118 | 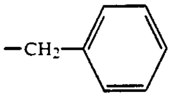 | $C_{11}H_{18}N_2O_2.HCl$ | 1.00~3.08(14H, m), 2.64~2.96(2H, bd), 3.44(2H, s), 3.32~3.48(2H, m), 3.80(3H, s), 6.76~7.52(9H, m) | B |
| 119 | 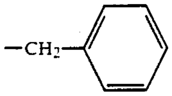 | $C_{12}H_{22}N_2O_2.HCl$ | 1.00~3.08(14H, m), 2.60(3H, s), 3.24~3.62 (2H, bd), 3.46(2H, s), 6.16(1H, bt), 7.26(5H, s), 7.08~8.00(4H, bd) | B |
| 120 | 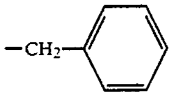 | $C_{22}H_{28}N_2O.HCl$ | 1.04~2.12(14H, m), 2.36(3H, s), 2.68~2.96 (2H, bd), 3.28~3.56(2H, m), 3.44(2H, s), 6.00(1H, bt), 7.08~7.70(9H, m) | B |
| 121 | 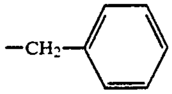 | $C_{23}H_{30}N_2O_2.HCl$ | 1.10~2.08(14H, m), 2.68~2.98(2H, bd), 3.28~3.56(2H, m), 3.46(2H, s), 3.88(3H, s), 3.89(3H, s), 5.94(1H, bt), 6.72~8.44(8H, m) | B |
| 122 | 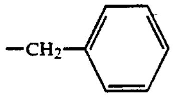 | $C_{18}H_{30}N_2O_2.HCl$ | 0.72~2.48(9H, m), 2.48~3.00(2H, bd), 3.48 (2H, s), 3.20~3.60(2H, m), 6.40~6.60(1H, bt), 7.08~7.92(14H, m) | B |
| 123 | 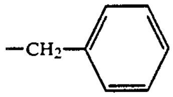 | $C_{17}H_{30}N_2O.HCl$ | 1.12~3.12(9H, m), 2.68~3.00(2H, bd), 3.32~3.62(2H, m), 3.46(2H, s), 6.06(1H, bt), 7.12~7.88(14H, m) | B |

TABLE 2-continued $R^1$—X—(A)—$R^2$

| | | | | |
|---|---|---|---|---|
| 124 | 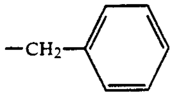 | $C_{11}H_{30}N_2O_3$.HCl | 0.92~3.08(14H, m), 2.64~2.98(2H, bd), 3.45(2H, s), 3.24~3.60(2H, m), 6.24(1H, bt), 7.04~8.28(14H, m) | B |
| 125 | 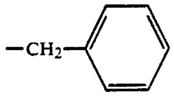 | $C_{23}H_{28}N_2O$.HCl | 0.96~2.08(14H, m), 2.68~2.96(2H, bd), 3.44(2H, s), 3.28~3.62(2H, m), 3.26(1H, bt), 7.08~8.28(12H, m) | B |
| 126 | 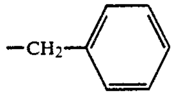 | $C_{20}H_{21}N_3O$.HCl | 1.2~2.06(7H, m), 2.80~2.92(2H, bd), 3.33~3.6(2H), 3.46(2H, s), 7.27(5H, s), 7.3~8.54(5H, m) | B |
| 127 | 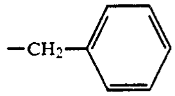 | $C_{21}H_{21}N_2OF$.HCl | 1.04~2.10(14H, m), 2.68~2.38(2H, bd), 3.46(2H, s), 3.24~3.56(2H, m), 6.06(1H, bt), 6.88~7.84(9H, m) | B |
| 128 | 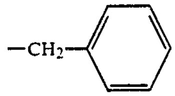 | $C_{13}H_{30}N_2O_2$.HCl | 0.96~3.08(14H, m), 2.60~3.03(2H, bd), 2.97(3H, s), 3.03~3.60(2H, m), 3.45(3H, S), 3.79(3H, s), 6.72~7.40(9H, m) | B |
| 129 | 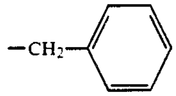 | $C_{27}H_{34}N_2O_2$.HCl.½$H_2O$ | 1.04~2.04(9H, m), 2.80(2H, broad d), 2.98 (3H, d), 3.20~3.48(2H, m), 3.24(2H, s), 5.06(2H, s), 6.90(2H, d), 7.16~7.44(12H, m) | B |
| 130 | 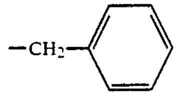 | $C_{30}H_{31}N_2O_2S$.HCl.½$H_2O$ | 0.92~1.96(12H, m), 2.60~3.54(8H, m), 4.36(2H, s), 6.96~7.44(12H, m), 7.60(2H, d) | B |
| 131 | 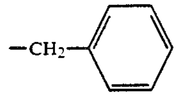 | $C_{18}H_{22}N_3O$ | 1.2~2.08(7H, m), 2.82~2.95(2H, bd), 3.27~3.4(2H, t), 3.48(2H, s), 6.4(1H), 7.26(5H, s), 7.53~7.60(2H), 8.65~8.73 (2H) | B |
| 132 | 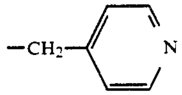 | $C_{27}H_{27}N_2O_2$.2HCl | 1.04~2.20(14H, m), 2.64~2.95(2H, bd), 3.32~3.64(2H, m), 3.46(2H, s), 6.48(1H, bt), 7.12~8.56(13H, m) | B |
| 133 | 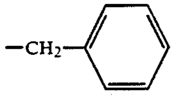 | $C_{12}H_{22}N_2O_2Cl$ | 1.07~2.50(9H, m), 2.71~2.82(2H, bd), 3.36(2H, s), 3.5~3.67(2H, t), 7.16(5H, s), 7.46~7.76(3H, m) | C |
| 134 | 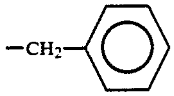 | $C_{22}H_{27}N_3O_3$ | 1.05~2.05(9H, m), 2.80~3.1(5H, m), 3.50(2H, d), 7.35(5H, s), 7.60(2H, d), 8.30(2H, d), | B |
| 135 | 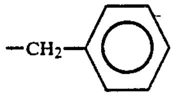 | $C_{23}H_{29}N_3O_3$ | 1.05~2.0(9H, m), 3.2(2H, d), 3.45(2H, d), 7.30(5H, s), 7.50(2H, d), | B |
| 136 | 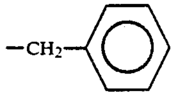 | $C_{22}H_{27}N_3O$ | 1.0~2.0(9H, m), 2.65~3.05, (5H, m), 3.45(2H, s), 7.30(5H, s), 7.45(2H, d), 7.70(2H, d), 8.30(2H, d), | B |

TABLE 2-continued

| $R^1$—X—Ⓐ—$R^2$ | | | | |
|---|---|---|---|---|
| 137 | 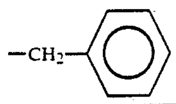 | $C_{23}H_{29}N_3O$ | 1.0~2.0(9H, m), 2.8(2H, d), 3.15(2H, d), 3.45(2H, s), 7.30(5H, s), 7.35(2H, d), 7.60(2H, d), | B |

In order to show the effects of the compounds of the invention in detail, part of examples of pharmacological experiments using animals will be described hereinunder.

In addition to the working examples disclosed above in view of the pharmacological tests, the compound of the invention was examined in view of effects on scopolamine-induced impairment of passive avoidance, using ddY male mice. As a result it was found that it had an excellent activity in this respect.

EXPERIMENTAL EXAMPLE 1

Acetylcholinesterase Inhibitory Action using Mouse Brain Homogenate

Using a mouse brain homogenate as a source of acetylchlolinesterase, the esterase activity was measured by a thiocholine method. Acetylcholine as a substrate, the compound of the invention as a substance to test and 5,5'-dithio-bis(2-nitrobenzoic acid), called also DTNB, were added to the mouse brain homogenate. After incubation, thiocholine produced was reacted with DTNB to form a yellow product. The acetylcholinesterase activity was determined by the measurement of the absorbance change of the reaction product at 412 nm.

The acetylcholinesterase inhibitory activity of the compound tested was expressed in terms of the 50% inhibitory concentration, IC50.

Results are shown in Table 3.

TABLE 3

| Compound (Example No.) | AchE inhibitory activity $IC_{50}$ (μM) |
|---|---|
| 4 | 0.0006 |
| 5 | 0.088 |
| 6 | 0.021 |
| 7 | 0.014 |
| 8 | 0.08 |
| 9 | 0.0055 |
| 10 | 0.0042 |
| 16 | 0.059 |
| 21 | 0.021 |
| 25 | 0.0045 |
| 26 | 0.009 |
| 32 | 0.0043 |
| 41 | 0.0008 |
| 47 | 0.009 |
| 48 | 0.0039 |
| 50 | 0.0028 |
| 51 | 0.0022 |
| 52 | 0.0015 |
| 53 | 0.0024 |
| 54 | 0.008 |
| 56 | 0.0033 |
| 57 | 0.0012 |
| 58 | 0.013 |
| 62 | 0.0034 |
| 68 | 0.0045 |
| 71 | 0.055 |
| 88 | 0.049 |
| 98 | 0.0083 |
| 110 | 0.0088 |
| 111 | 0.00088 |
| 112 | 0.00015 |

TABLE 3-continued

| Compound (Example No.) | AchE inhibitory activity $IC_{50}$ (μM) |
|---|---|
| 113 | 0.0047 |
| 115 | 0.0067 |
| 116 | 0.009 |
| 122 | 0.02 |
| 123 | 0.0105 |
| 130 | 0.0003 |
| 133 | 0.0079 |
| Physo *1 | 0.89 |
| THA *2 | 0.084 |

(Notes)
*1: physostigmine
*2: 1,2,3,4-Tetrahydro-9-Aminoacridine

EXPERIMENTAL EXAMPLE 2

Acute Toxicity Test for ddY Male Mouse

Acute toxicity test was carried out using ddY male mice.

The results are shown in Table 4.

TABLE 4

| Compound (Example No.) | Oral to mouse (mg/kg) 100 mg | 300 mg |
|---|---|---|
| 4 | 0/3 *1 | 2/4 *1 |
| 5 | 1/4 | 4/4 |
| 7 | — | 0/3 |
| 10 | 3/4 | — |

(Notes)
*1: Denominator shows the number of Animals used, and numerator shows the number of deaths.

What is claimed is:

1. A piperidine derivative having the formula (I) or a pharmacologically acceptable salt thereof:

$$R^1—X—A—R^2 \quad (I)$$

wherein $R^1$ is pyrazinedicarboxylic acid imide,

X is $—(CH_2)_n—$, $—O(CH_2)_n—$, $—S(CH_2)_n—$, $—NH(CH_2)_n—$, $—SO_2NH(CH_2)_n—$,

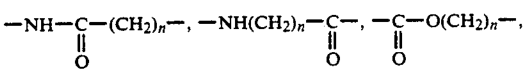

$—CH_2NH(CH_2)_n—$,

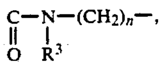

wherein n is an integer of 1 through 7 and $R^3$ is hydrogen, lower alkyl or benzyl,

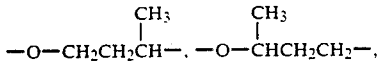

—O—$CH_2CH_2CH$= or

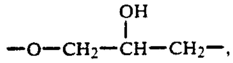

A is

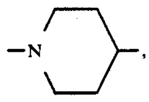 , 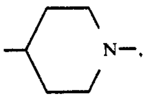 ,

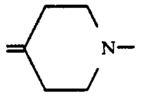 or 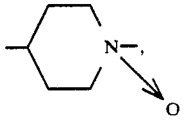

and $R^2$ is hydrogen, lower alkyl, benzyl, benzyl substituted by hydroxy, methoxy or 1 or 2 chloro, benzoyl, benzoyl substituted by fluoro, pyridyl, 2-hydroxyethyl, pyridylmethyl or a group of the formula

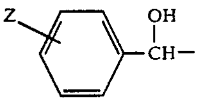

wherein Z represents a halogen atom.

2. A piperidine derivative having the formula (I) or a pharmacologically acceptable salt thereof:

$$R^1—X—A—R^2 \qquad (I)$$

wherein $R^1$ is pyrazinedicarboxylic acid imide,

X is $—(CH_2)_n—$, $—O(CH_2)_n—$, $—S(CH_2)_n—$, $—NH(CH_2)_n—$, $—SO_2NH(CH_2)_n—$,

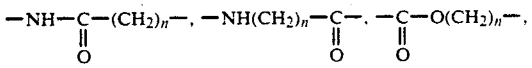

$—CH_2NH(CH_2)_n—$, (wherein n is an integer of 1 through 7 and $R^3$ is hydrogen, lower alkyl or benzyl),

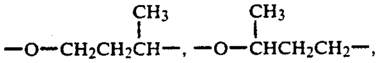

—O—$CH_2CH_2CH$= or

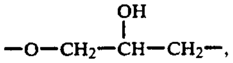

A is

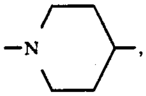 , 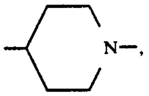 ,

-continued

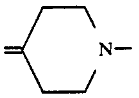 or 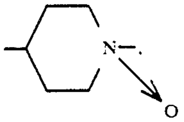

and $R^2$ is hydrogen, lower alkyl, benzyl, benzyl substituted by hydroxy, methoxy or 1 or 2 chloro, benzoyl, benzoyl substituted by fluoro, pyridyl, 2-hydroxyethyl, pyridylmethyl or

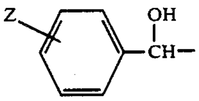

wherein Z represents a halogen atom.

3. A piperidine derivative or a pharmacologically acceptable salt thereof as claimed in claim 1, in which x is $—(CH_2)_n—$.

4. A piperidine derivative or a pharmacologically acceptable salt thereof as claimed in claim 2, in which X is $—(CH_2)_n—$.

5. A piperidine derivative or a pharmacologically acceptable salt thereof as claimed in claim 1, in which X is

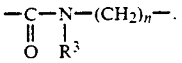

6. A piperidine derivative or a pharmacologically acceptable salt thereof as claimed in claim 1, in which the ring A is

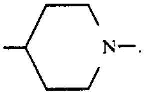

7. A piperidine derivative or a pharmacologically acceptable salt thereof as claimed in claim 2, in which the ring A is

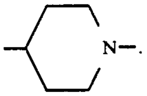

8. A piperidine derivative or a pharmacologically acceptable salt thereof as claimed in claim 1, in which X is

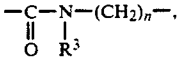

and A is

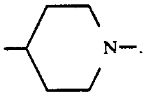

9. A piperidine derivative or a pharmacologically acceptable salt thereof as claimed in claim 8, in which $R^2$ is benzyl or benzyl substituted with hydroxy, methoxy or 1 or 2 chloro.

10. A piperidine derivative or a pharmacologically acceptable salt thereof as claimed in claim 1, in which n is 2.

11. A piperidine derivative or a pharmacologically acceptable salt thereof as claimed in claim 2, in which n is 2.

12. A pharmaceutical composition which comprises the piperidine derivative as defined in claim 1 and a pharmacologically acceptable carrier.

13. A pharmaceutical composition which comprises the piperidine derivative as defined in claim 2 and a pharmacologically acceptable carrier.

14. A method for treating dementias and sequelae of cerebrovascular diseases which comprises administering to a patient requiring such treatment a pharmacologically effective amount of the piperidine derivative as defined in claim 1.

15. A method for treating dementias and sequelae of cerebrovascular diseases which comprises administering to a patient requiring such treatment a pharmacologically effective amount of the piperidine derivative as defined in claim 2.

* * * * *

UNITED STATES PATENT AND TRADEMARK OFFICE
CERTIFICATE OF CORRECTION

PATENT NO. : 5 118 684

DATED : June 2, 1992

INVENTOR(S) : Hachiro SUGIMOTO et al

It is certified that error appears in the above-identified patent and that said Letters Patent is hereby corrected as shown below:

On title page, item [57], line 2; change "slt" to ---salt---.

Signed and Sealed this

Twenty-eighth Day of September, 1993

Attest:

BRUCE LEHMAN

Attesting Officer

*Commissioner of Patents and Trademarks*